US011796446B2

United States Patent
Ko et al.

(10) Patent No.: US 11,796,446 B2
(45) Date of Patent: Oct. 24, 2023

(54) SYSTEMS AND METHODS FOR AUTOMATED HEMATOLOGICAL ABNORMALITY DETECTION

(71) Applicant: National Taiwan University, Taipei (TW)

(72) Inventors: Bor-Sheng Ko, Taipei (TW); Yu-Fen Wang, Taipei (TW); Chi-Chun Lee, Hsinchu (TW); Jeng-Lin Li, Hsinchu (TW); Jih-Luh Tang, Taipei (TW)

(73) Assignee: National Taiwan University, Taipei (TW)

( * ) Notice: Subject to any disclaimer, the term of this patent is extended or adjusted under 35 U.S.C. 154(b) by 1013 days.

(21) Appl. No.: 16/590,335

(22) Filed: Oct. 1, 2019

(65) Prior Publication Data

US 2021/0096054 A1 Apr. 1, 2021

(51) Int. Cl.
*G01N 15/14* (2006.01)
*G06N 20/10* (2019.01)
(Continued)

(52) U.S. Cl.
CPC ......... *G01N 15/1459* (2013.01); *G01N 15/14* (2013.01); *G01N 33/574* (2013.01);
(Continued)

(58) Field of Classification Search
CPC .............. G06T 7/0012; G06V 10/10; G06V 2201/034; G06V 40/197; G06V 10/82
See application file for complete search history.

(56) References Cited

U.S. PATENT DOCUMENTS

| 8,682,810 B2 * | 3/2014 | Zhang | G06V 20/698 382/128 |
| 2002/0141625 A1 * | 10/2002 | Nelson | G01N 23/046 382/131 |

(Continued)

FOREIGN PATENT DOCUMENTS

WO WO-2007003017 A1 * 1/2007 ........... C12Q 1/6816

OTHER PUBLICATIONS

Bor-Sheng et al., "Clinically validated machine learning algorithm for detecting residual diseases with multicolor flow cytometry analysis in acute myeloid leukemia and myelodysplastic syndrome", Oct. 22, 2018, EBioMedicine 37 (2018) 91-100, pp. 91-100, provided by Applicant via IDS.*

(Continued)

*Primary Examiner* — Guillermo M Rivera-Martinez
(74) *Attorney, Agent, or Firm* — Perkins Coie LLP; Han-Wei Chen; Andrew T. Pettit

(57) ABSTRACT

This application relates generally to automated systems and associated methods for identifying hematological abnormalities. An automated system can include at least one processor that, in operation, is configured to: receive, from a flow cytometer, a flow cytometry data matrix characterizing a tube that is associated with a sample; convert the flow cytometry data matrix into a high dimensional vector; produce a single sample high dimensional vector including a concatenation of multiple high dimensional vectors associated with the sample, wherein the multiple high dimensional vectors comprise the tube high dimensional vector; assemble a training data set including multiple sample high dimensional vectors; receive, from a datastore, outcome information including respective labels associated with each of the multiple sample high dimensional vectors; and train a classifier
(Continued)

sifier based on the training data set and the outcome information.

19 Claims, 21 Drawing Sheets

(51) Int. Cl.
    *G01N 33/574*     (2006.01)
    *G16B 50/30*     (2019.01)
    *G06F 18/2115*     (2023.01)

(52) U.S. Cl.
    CPC ......... *G06F 18/2115* (2023.01); *G06N 20/10* (2019.01); *G16B 50/30* (2019.02); *G01N 2015/1488* (2013.01)

(56) References Cited

U.S. PATENT DOCUMENTS

| | | | | |
|---|---|---|---|---|
| 2003/0044968 A1* | 3/2003 | Lafferty | ............. | C12N 15/1037 702/19 |
| 2003/0219752 A1* | 11/2003 | Short | ................... | C12Q 1/6881 435/7.1 |
| 2008/0221711 A1* | 9/2008 | Trainer | ............... | G01N 15/1459 356/338 |
| 2015/0198591 A1* | 7/2015 | Patel | .................. | G01N 33/6854 435/7.25 |
| 2018/0017525 A1* | 1/2018 | Gordon | ............ | G01N 27/44791 |
| 2018/0046883 A1* | 2/2018 | Soomro | ................ | G06T 7/0012 |
| 2018/0247195 A1* | 8/2018 | Kumar | ..................... | G06N 3/08 |
| 2018/0247715 A1* | 8/2018 | Kumar | ................... | G16H 15/00 |

OTHER PUBLICATIONS

BS. Ko, et al. "Clinically validated machine learning algorithm for detecting residual diseases with multicolor flow cytometry analysis in acute myeloid leukemia and myelodysplastic syndrome," EBioMedicine. Nov. 2018; 37:91-100.

DS. Frankel, et al., "Application of Neural Networks to Flow Cytometry Data Analysis and Real-Time Cell Classification," Cytometry, Apr. 1, 1996; 23(4):290-302.

HT. Salah, et al., "Machine learning applications in the diagnosis of leukemia: Current trends and future directions," Int. J. Lab Hematol. Dec. 2019;41(6):717-725.

T. Pham, et al., "Predicting healthcare trajectories from medical records: A deep learning approach," J Biomed. Inform. May 2017; 69:218-229.

* cited by examiner

SYSTEMS AND METHODS FOR AUTOMATED HEMATOLOGICAL ABNORMALITY DETECTION

BACKGROUND

This application relates generally to automated systems and methods to identify hematological abnormalities.

Hematological abnormalities, such as acute myeloid leukemia (AML) and myelodysplastic syndrome (MDS), may be characterized by abnormal proliferation of myeloid progenitors and subsequent bone marrow failure. Existence of minimal (or measurable) residual disease (MRD), which refers to leukemic cells detected below the threshold for morphological recognition (e.g., about 0.1%), may be a valuable marker for evaluating the response after treatment, and now serves as an important prognostic indicator for AML. Multiparameter flow cytometry (MFC) may detect minimal residual disease (MRD) and stratify prognosis in AML and MDS after therapy.

SUMMARY

The exemplary embodiments disclosed herein are directed to solving the issues relating to one or more of the problems presented in the prior art, as well as providing additional features that will become readily apparent by reference to the following detailed description when taken in conjunction with the accompanied drawings. In accordance with various embodiments, exemplary systems, methods, devices and computer program products are disclosed herein. It is understood, however, that these embodiments are presented by way of example and not limitation, and it will be apparent to those of ordinary skill in the art who read the present disclosure that various modifications to the disclosed embodiments can be made while remaining within the scope of the invention.

In certain embodiments, a system includes at least one processor operatively coupled with a datastore, the at least one processor configured to: receive, from a flow cytometer, a flow cytometry data matrix characterizing a tube, wherein the tube is associated with a sample; convert the flow cytometry data matrix into a tube high dimensional vector; produce a single sample high dimensional vector including a concatenation of multiple high dimensional vectors associated with the sample, wherein the multiple high dimensional vectors include the tube high dimensional vector; assemble a training data set including multiple sample high dimensional vectors, wherein the multiple sample high dimensional vectors include the single sample high dimensional vector; receive, from the datastore, outcome information including respective labels associated with each of the multiple sample high dimensional vectors; and train a classifier based on the training data set and the outcome information.

In certain embodiments, the at least one processor is further configured to: determine an outcome for a new sample based on applying the classifier to the new sample.

In certain embodiments, the at least one processor is further configured to: determine an outcome for a new sample based on applying the classifier to a new single sample high dimensional vector associated with the new sample.

In certain embodiments, the sample is derived from blood, mucus, or bone marrow from a person.

In certain embodiments, the respective labels characterize whether each of the multiple sample high dimensional vectors are normal or abnormal.

In certain embodiments, the respective labels characterize whether each of the multiple sample high dimensional vectors are indicative of a hematological malignancy.

In certain embodiments, the classifier is trained using support vector machines.

In certain embodiments, the at least one processor is further configured to: convert the flow cytometry data matrix into the tube high dimensional vector using a python toolkit or other suitable means such as Fisher vector encoding and a gaussian mixture model distribution.

In certain embodiments, the at least one processor is further configured to: convert the flow cytometry data matrix into the tube high dimensional vector by modeling the flow cytometry data matrix with a generative probability distribution.

In certain embodiments, a method performed by a computing device, includes: separating a sample set into a training data set and a validation data set; receiving a flow cytometry data matrix characterizing a tube, wherein the tube is associated with a sample; converting the flow cytometry data matrix into a tube high dimensional vector; producing a single sample high dimensional vector including a concatenation of multiple high dimensional vectors associated with the sample, wherein the multiple high dimensional vectors include the tube high dimensional vector; assembling the training data set including multiple sample high dimensional vectors, wherein the multiple sample high dimensional vectors include the single sample high dimensional vector; receiving training outcome information including respective training outcome labels for each of the multiple sample high dimensional vectors; training a classifier based on the training data set and the training outcome information; receiving validation outcome information including respective validation outcome labels of the validation data set; and determining an accuracy value for the classifier based on the validation data set and the validation outcome information.

In certain embodiments, each of the multiple high dimensional vectors are associated with respective tubes of the sample.

In certain embodiments, each of the multiple sample high dimensional vectors are associated with respective samples.

In certain embodiments, the concatenation of multiple high dimensional vectors is produced in a predetermined manner of concatenation.

In certain embodiments, each of the multiple sample high dimensional vectors are produced in accordance with the predetermined manner of concatenation.

In certain embodiments, the computing device is a flow cytometer.

In certain embodiments, a non-transitory computer readable medium has instructions stored thereon, wherein the instructions, when executed by a processor, cause a device to perform operations including: receiving a flow cytometry data matrix characterizing a tube, wherein the tube is associated with a sample; converting the flow cytometry data matrix into a tube high dimensional vector; producing a single sample high dimensional vector including a concatenation of multiple high dimensional vectors associated with the sample, wherein the multiple high dimensional vectors include the tube high dimensional vector; assembling a training data set including multiple sample high dimensional vectors, wherein the multiple sample high dimensional vectors include the single sample high dimensional vector;

receiving outcome information including respective labels associated with each of the multiple sample high dimensional vectors; and training a classifier based on the training data set and the outcome information.

In certain embodiments, the operations further include: receiving the flow cytometry data matrix from over a network.

In certain embodiments, the operations further include: determining an accuracy value for the classifier based on a validation data set and validation outcome information.

In certain embodiments, the validation data set includes multiple validation high dimensional vectors associated with validation samples and the validation outcome information includes respective validation outcome labels associated with each of the multiple validation high dimensional vectors.

In certain embodiments, the operations further include: training the classifier based on an expanded training data set with a greater number of samples than the training data set in response to the accuracy value falling below a threshold value.

BRIEF DESCRIPTION OF THE DRAWINGS

Various exemplary embodiments of the invention are described in detail below with reference to the following Figures. The drawings are provided for purposes of illustration only and merely depict exemplary embodiments of the invention. These drawings are provided to facilitate the reader's understanding of the invention and should not be considered limiting of the breadth, scope, or applicability of the invention. It should be noted that for clarity and ease of illustration these drawings are not necessarily drawn to scale.

DETAILED DESCRIPTION OF EXEMPLARY EMBODIMENTS

Figure 1:
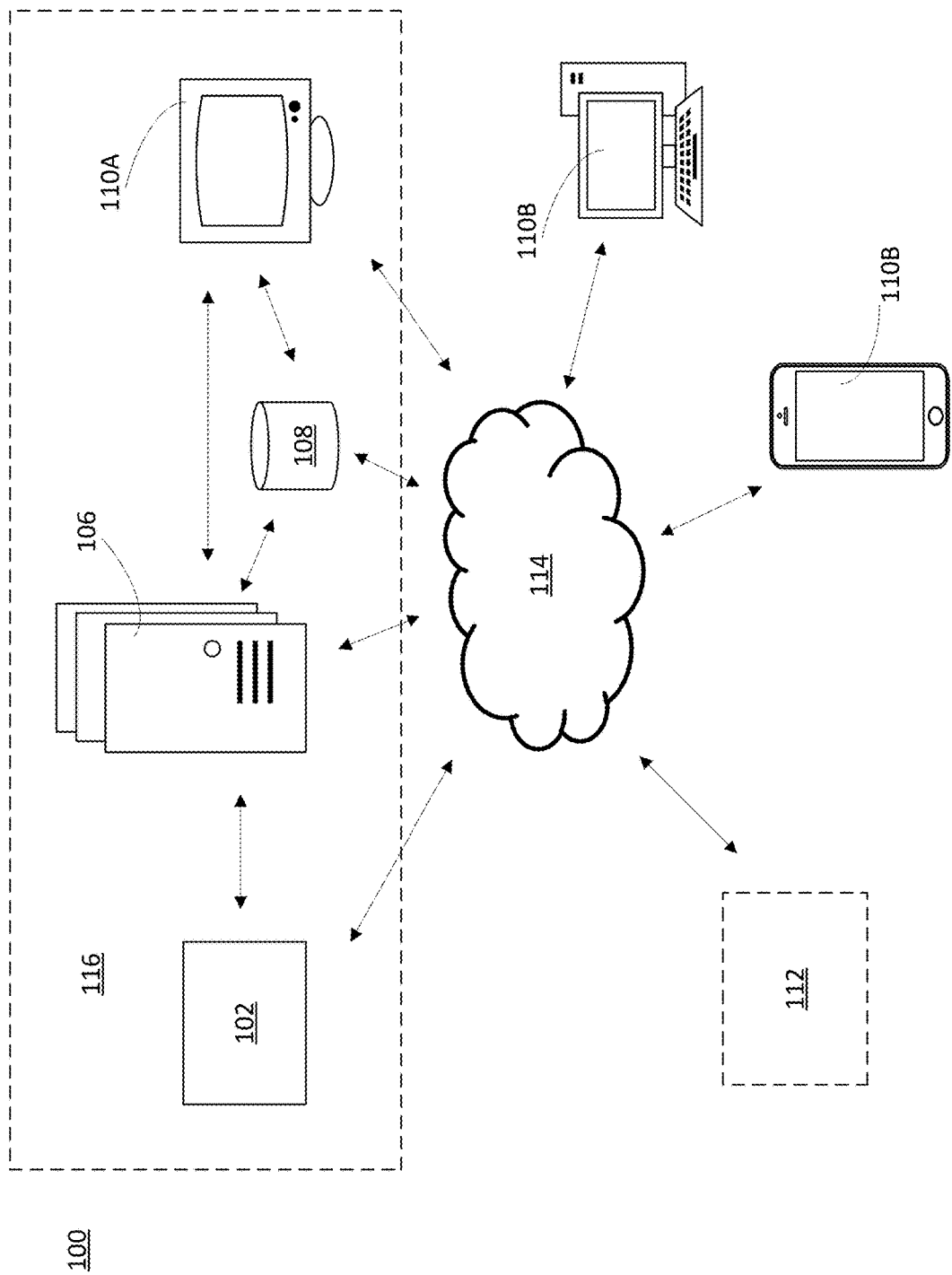
FIG. 1 is a system diagram illustrating features of automated hematological abnormality detection system, in accordance with certain embodiments.

Current MFC presents drawbacks such as lack of inter-lab standardization, and painstaking manual gating process involving serial projections of two-dimensional attributes.

Examples of MFC analysis approaches for leukemia MRD detection may include a leukemia-associated aberrant immune-phenotype (LAIP) approach and a "difference from normal" approach. The LAIP approach may assay MRD under the assumption that the residual disease possesses the phenotype identical to the initial one, and therefore is dependent on individually selected antibody combination panels according to leukemia phenotype identified at diagnosis. In contrast, the "difference from normal" approach may use a standardized panel of antibodies for all specimens and distinguishes abnormal residual leukemic cells from normal ones with established immunophenotypic profiles. Therefore, the "difference from normal" approach does not require knowledge of the phenotype at diagnosis for the MRD detection. Although more biologically reasonable, the LAIP approach risks in higher false negative MRD rates due to altered antigen expression from clonal evolution during disease progression. Furthermore, the quality of both approaches depends highly on experienced physicians, and individual idiosyncrasy inevitably affects diagnostic reproducibility and objectivity. In addition, manual gating is time-consuming and infeasible to obtain information from the multivariate measurement data due to it observational nature. Therefore, traditional manual MFC analysis approaches for leukemia MRD detection may not be entirely satisfactory.

Various exemplary embodiments of the invention are described below with reference to the accompanying figures to enable a person of ordinary skill in the art to make and use the invention. As would be apparent to those of ordinary skill in the art, after reading the present disclosure, various changes or modifications to the examples described herein can be made without departing from the scope of the invention. Thus, the present invention is not limited to the exemplary embodiments and applications described and illustrated herein. Additionally, the specific order or hierarchy of steps in the methods disclosed herein are merely exemplary approaches. Based upon design preferences, the specific order or hierarchy of steps of the disclosed methods or processes can be rearranged while remaining within the scope of the present invention. Thus, those of ordinary skill in the art will understand that the methods and techniques disclosed herein present various steps or acts in a sample order, and the invention is not limited to the specific order or hierarchy presented unless expressly stated otherwise.

In contrast with the manual MFC analysis approaches for leukemia MRD detection referenced above, a reliable automated MFC analysis can improve healthcare quality by providing rapid clinical decision diagnosis and support. Accordingly, systems and methods in accordance with various embodiments include automated hematological abnormality detection that utilizes a hematological abnormality classifier for a multi-dimensional MFC phenotype trained using, for example, support vector machines (SVM) after gaussian mixture model (GMM) modeling. In some embodiments, this hematological abnormality classifier represents a supervised machine learning (SML) technique in analyzing a MFC dataset to develop an automated MFC interpretation for detecting MRD objectively in AML and MDS patients. SML refers to a branch of artificial intelligence (AI) that describes learning from data and expert provided labels to generate reliable automated inference. Rather than using a predefined model, in some embodiments, SML performs inferences by learning the underlying patterns (functional mapping) between measurement data and desirable outcome variables with large-scale data. As will be discussed in detail below, the hematological abnormality classifier may produce good accuracies (e.g., 84.6% to 92.4%) and a good area under the receiver operating characteristic (ROC) curve (AUC) (e.g., 0.921-0.950).

FIG. 1 is a system diagram illustrating features of automated hematological abnormality detection system 100, in accordance with certain embodiments. An automated hematological abnormality detection system 100 may include a flow cytometer 102 (e.g., an MFC device), a detection server 106 (implemented as one or more servers), a datastore 108, a local user device 110A, remote user devices 110B, and a remote flow cytometer 112 (e.g., a remote MFC device). In certain embodiments, each of the flow cytometer 102, detection server 106, datastore 108, local user device 110A, remote user devices 110B, and remote flow cytometer 112 may be connected via a network 114 (e.g., the Internet) or via local connections (e.g., communications interfaces).

In various embodiments, the functionality of each of the detection server 106, datastore 108, and local user device 110 may be implemented in a single remote server and/or locally on a user device. In further embodiments, the functionality of each of the flow cytometer 102, detection server 106, datastore 108, and local user device 110 may be implemented in a single flow cytometer and referred to as a combined flow cytometer 116 (e.g., within a single housing). Furthermore, in particular embodiments, each of each of the flow cytometer 102, detection server 106, datastore 108, and local user device 110 may be communicatively coupled with each other directly. Also, the detection server 106, in whole or in part, may be communicatively coupled over the network 114 to a variety of external devices. These external devices may include, for example, the remote user devices 110B and/or remote flow cytometer 112.

Figure 2:
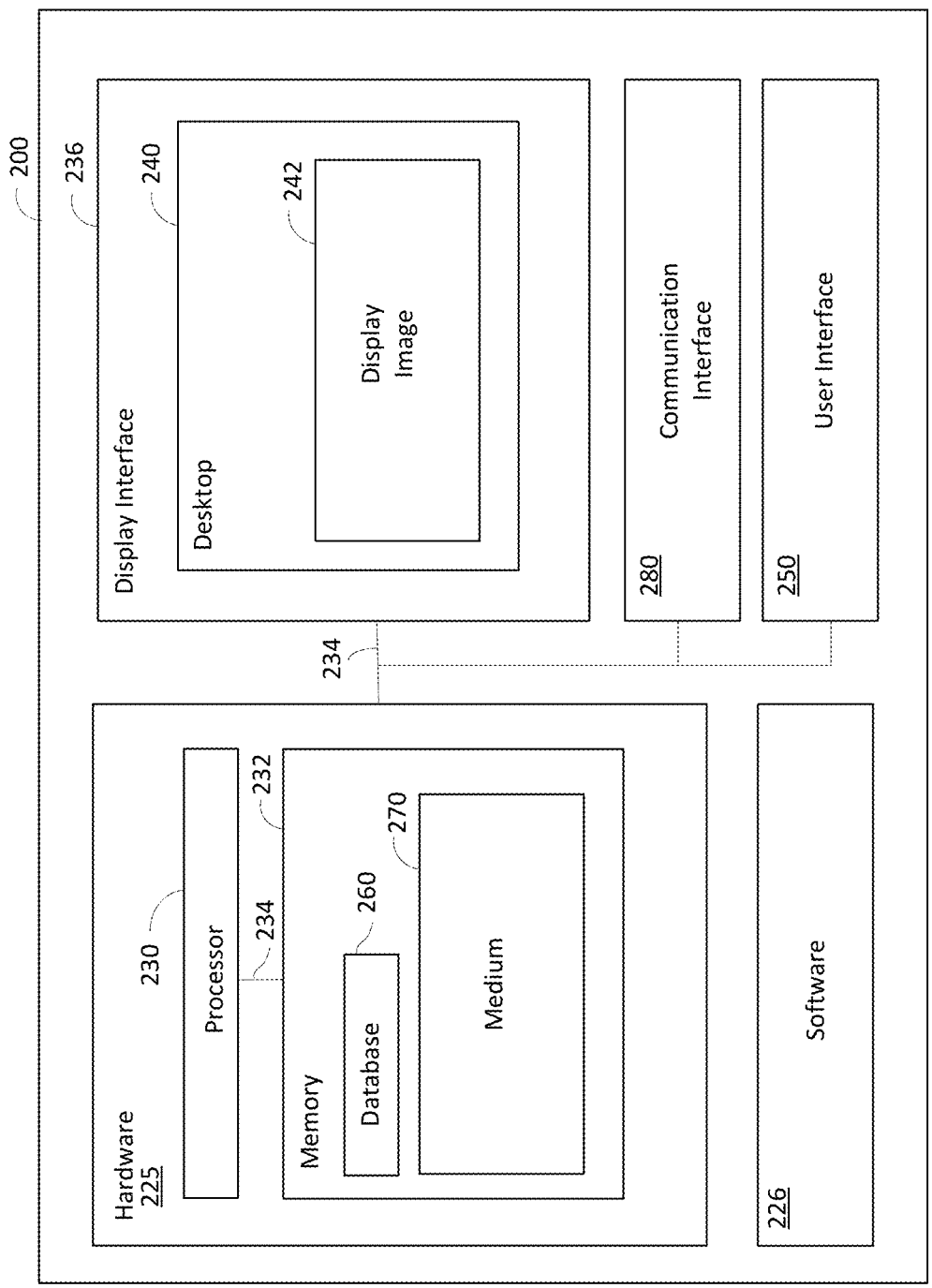
FIG. 2 is a block diagram of an exemplary computing device, in accordance with various embodiments.

FIG. 2 is a block diagram of an exemplary computing device 200, in accordance with various embodiments. As noted above, the computing device 200 may represent exemplary components of a particular flow cytometer (whether remote or local), detection server, and/or user device (whether remote or local). In some embodiments, the computing device 200 includes a hardware unit 225 and software 226. Software 226 can run on hardware unit 225 (e.g., the processing hardware unit) such that various applications or programs can be executed on hardware unit 225 by way of software 226. In some embodiments, the functions of software 226 can be implemented directly in hardware unit 225 (e.g., as a system-on-a-chip, firmware, field-programmable gate array ("FPGA"), etc.). In some embodiments, hardware unit 225 includes one or more processors, such as processor 230. In some embodiments, processor 230 is an execution unit, or "core," on a microprocessor chip. In some embodiments, processor 230 may include a processing unit, such as, without limitation, an integrated circuit ("IC"), an ASIC, a microcomputer, a programmable logic controller ("PLC"), and/or any other programmable circuit. Alternatively, processor 230 may include multiple processing units (e.g., in a multi-core configuration). The above examples are exemplary only, and, thus, are not intended to limit in any way the definition and/or meaning of the term "processor." Hardware unit 225 also includes a system memory 232 that is coupled to processor 230 via a system bus 234. Memory 232 can be a general volatile RAM. For example, hardware unit 225 can include a 32 bit microcomputer with 2 Mbit ROM and 64 Kbit RAM, and/or a number of GB of RAM. Memory 232 can also be a ROM, a network interface (NIC), and/or other device(s).

In some embodiments, the system bus 234 may couple each of the various system components together. It should be noted that, as used herein, the term "couple" is not limited to a direct mechanical, communicative, and/or an electrical connection between components, but may also include an indirect mechanical, communicative, and/or electrical connection between two or more components or a coupling that is operative through intermediate elements or spaces. The system bus 234 can be any of several types of bus structure(s) including a memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect Card International Association Bus (PCMCIA), Small Computers Interface (SCSI) or other proprietary bus, or any custom bus suitable for computing device applications.

In some embodiments, optionally, the computing device 200 can also include at least one media output component or display interface 236 for use in presenting information to a user. Display interface 236 can be any component capable of conveying information to a user and may include, without limitation, a display device (not shown) (e.g., a liquid crystal display ("LCD"), an organic light emitting diode ("OLED") display, or an audio output device (e.g., a speaker or headphones). In some embodiments, computing device 200 can output at least one desktop, such as desktop 240. Desktop 240 can be an interactive user environment provided by an operating system and/or applications running within computing device 200, and can include at least one screen or display image, such as display image 242. Desktop 240 can also accept input from a user in the form of device inputs, such as keyboard and mouse inputs. In some embodiments, desktop 240 can also accept simulated inputs, such as simulated keyboard and mouse inputs. In addition to user input and/or output, desktop 240 can send and receive device data, such as input and/or output for a FLASH memory device local to the user, or to a local printer.

In some embodiments, the computing device 200 includes an input or a user interface 250 for receiving input from a user. User interface 250 may include, for example, a keyboard, a pointing device, a mouse, a stylus, a touch sensitive panel (e.g., a touch pad or a touch screen), a gyroscope, an accelerometer, a position detector, and/or an audio input device. A single component, such as a touch screen, may function as both an output device of the media output component and the input interface. In some embodiments, mobile devices, such as tablets, can be used.

In some embodiments, the computing device 200 can include a database 260 within memory 232, such that various information can be stored within database 260. Alternatively, in some embodiments, database 260 can be included within a remote datastore (not shown) or a remote server (not shown) with file sharing capabilities, such that database 260 can be accessed by computing device 200 and/or remote end users. In some embodiments, a plurality of computer-executable instructions can be stored in memory 232, such as one or more computer-readable storage medium 270 (only one being shown in FIG. 2). Computer-readable storage medium 270 includes non-transitory media and may include volatile and nonvolatile, removable and non-removable mediums implemented in any method or technology for storage of information such as computer-readable instructions, data structures, program modules or other data. The instructions may be executed by processor 230 to perform various functions described herein.

In the example of FIG. 2, the computing device 200 can be a communication device, a storage device, or any device capable of running a software component. For non-limiting examples, the computing device 200 can be but is not limited to a flow cytometer, a server machine, smartphone, a laptop PC, a desktop PC, a tablet, a Google's Android device, an iPhone, an iPad, and a voice-controlled speaker or controller.

The computing device 200 has a communications interface 280, which enables the computing devices to communicate with each other, the user, and other devices over one or more communication networks following certain communication protocols, such as TCP/IP, http, https, ftp, and sftp protocols. Here, the communication networks can be but are not limited to, the Internet, an intranet, a wide area network (WAN), a local area network (LAN), a wireless network, Bluetooth, WiFi, and a mobile communication network.

In some embodiments, the communications interface 280 may include any suitable hardware, software, or combination of hardware and software that is capable of coupling the computing device 200 to one or more networks and/or additional devices. The communications interface 280 may be arranged to operate with any suitable technique for controlling information signals using a desired set of communications protocols, services or operating procedures. The communications interface 280 may comprise the appropriate physical connectors to connect with a corresponding communications medium, whether wired or wireless.

A network may be utilized as a vehicle of communication. In various aspects, the network may comprise local area networks (LAN) as well as wide area networks (WAN) including without limitation the Internet, wired channels, wireless channels, communication devices including telephones, computers, wire, radio, optical or other electromagnetic channels, and combinations thereof, including other devices and/or components capable of/associated with communicating data. For example, the communication environments comprise in-body communications, various devices, and various modes of communications such as wireless communications, wired communications, and combinations of the same.

Wireless communication modes comprise any mode of communication between points (e.g., nodes) that utilize, at least in part, wireless technology including various protocols and combinations of protocols associated with wireless transmission, data, and devices. The points comprise, for example, wireless devices such as wireless headsets, audio and multimedia devices and equipment, such as audio players and multimedia players, telephones, including mobile telephones and cordless telephones, and computers and computer-related devices and components, such as printers, network-connected machinery, and/or any other suitable device or third-party device.

Wired communication modes comprise any mode of communication between points that utilize wired technology including various protocols and combinations of protocols associated with wired transmission, data, and devices. The points comprise, for example, devices such as audio and multimedia devices and equipment, such as audio players and multimedia players, telephones, including mobile telephones and cordless telephones, and computers and computer-related devices and components, such as printers, network-connected machinery, and/or any other suitable device or third-party device. In various implementations, the wired communication modules may communicate in accordance with a number of wired protocols. Examples of wired protocols may comprise Universal Serial Bus (USB) communication, RS-232, RS-422, RS-423, RS-485 serial protocols, FireWire, Ethernet, Fibre Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, to name only a few examples.

Accordingly, in various aspects, the communications interface 280 may comprise one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the communications interface 280 may comprise a wireless interface comprising one or more antennas, transmitters, receivers, transceivers, amplifiers, filters, control logic, and so forth.

In various aspects, the communications interface 280 may provide data communications functionality in accordance with a number of protocols. Examples of protocols may comprise various wireless local area network (WLAN) protocols, including the Institute of Electrical and Electronics Engineers (IEEE) 802.xx series of protocols, such as IEEE 802.11a/b/g/n, IEEE 802.16, IEEE 802.20, and so forth. Other examples of wireless protocols may comprise various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols may comprise wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may comprise near-field communication techniques and protocols, such as electro-magnetic induction (EMI) techniques. An example of EMI techniques may comprise passive or active radio-frequency identification (RFID) protocols and devices. Other suitable protocols may comprise Ultra Wide Band (UWB), Digital Office (DO), Digital Home, Trusted Platform Module (TPM), ZigBee, and so forth.

Figure 3:
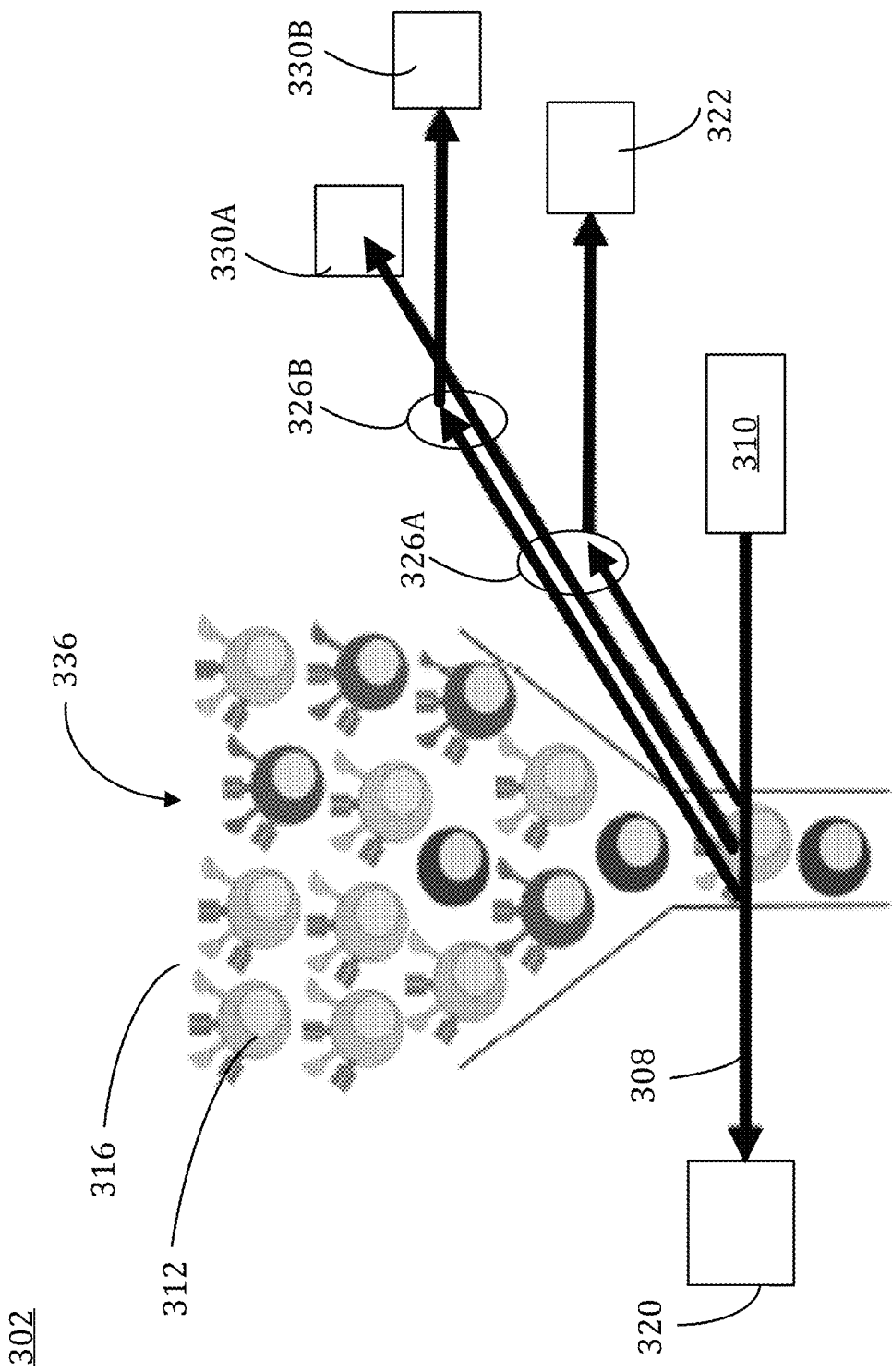
FIG. 3 illustrates aspects of a flow cytometer, in accordance with various embodiments.

FIG. 3 illustrates aspects of a flow cytometer 302, in accordance with various embodiments. The flow cytometer may also be referred to as a flow cytometry instrument or an MFC (multiparameter flow cytometry) device. The flow cytometer may analyze a tube of a sample and produce a flow cytometry data matrix as an output. Accordingly, flow cytometry is a technology for analyzing the physical and chemical characteristics of particles in a fluid that are passed in a stream 306 through the beam 308 of at least one laser 310. One way to analyze cell characteristics using flow cytometry is to label cells 312 with a fluorophore 314 and then excite the fluorophore 314 with the least one laser to emit light at the fluorophore emission frequency. The fluorescence is measured as cells 312 pass through one or more laser beams 310 simultaneously. Up to thousands of cells 312 per second can be analyzed as they pass through the laser beams 308 in the liquid stream 306. Characteristics of the cells, such as their granularity, size, fluorescent response, and internal complexity, can be measured.

Accordingly, a flow cytometer comprises three main systems: fluidics, optics, and electronics. The fluidic system may transport the cells 316 in the stream 306 of fluid through the laser beams 308 where they are illuminated. The optics system may be made up of lasers 310 which illuminate the cells 312 in the stream 306 as they pass through the laser light 308 and scatter the light from the laser 310. When a fluorophore is present on the cell 312, it will fluoresce at its characteristic frequency, which fluorescence is then detected via a lensing system. The intensity of the light in the forward scatter direction (e.g., as represented by forward scatter light 320) and side scatter direction (e.g., as represented by side scatter light 322) may be used to determine size and granularity (e.g., internal complexity) of the cell 312. Optical filters and beam splitters 326A, 326B may direct the various scattered light signals to the appropriate detectors 330A, 330B, which generate electronic signals proportional to the intensity of the light signals they receive. Data may be thereby collected on each cell, may be stored in computer memory, and then the characteristics of those cells can be analyzed based on their fluorescent and light scattering properties. The electronic system may convert the light signals detected into electronic pulses that can be processed by a computer. Information on the quantity and signal intensity of different subsets within the overall cell sample can be identified and measured.

In certain embodiments, the flow cytometer can process with up to 17 or ≥17 fluorescence markers simultaneously, in addition to 6 side and forward scattering properties. Therefore, the data may include up to 17 or at least 17, 18, 19, 20, 21, 22, 23, or more channels. Therefore, a single sample run can yield a large set of data for analysis.

In various embodiments, flow cytometry data may be presented in the form of single parameter histograms or as 2-dimensional plots of parameters, generally referred to as cytograms, which display two measurement parameters, one on the x-axis and one on the y-axis, and the cell count as a density (dot) plot or contour map. In some embodiments, certain parameters are side scattering (SSC) intensity, forward scattering (FSC) intensity, fluorescence, or the like. SSC and FSC intensity signals can be categorized as Area, Height, or Width signals (SSC-A, SSC-H, SSC-W and FSC-A, FSC-H, FSC-W) and represent the area, height, and width of the photo intensity pulse measured by the flow cytometer electronics. The area, height, and width of the forward and side scatter signals can provide information about the size and granularity, or internal structure, of a cell as it passes through the measurement lasers. In further embodiments, parameters, which consist of various characteristics of forward and side scattering intensity, and fluorescence intensity in particular channels, are used as axes for the histograms or cytograms. In some applications, biomarkers represent dimensions as well. Cytograms may display the data in various forms, such as a dot plot, a pseudo-color dot plot, a contour plot, or a density plot. The data can be used to count cells in particular populations by detection of biomarkers and light intensity scattering parameters. A biomarker may be detected when the intensity of the fluorescent emitted light for that biomarker reaches a particular threshold level.

As noted above, the flow cytometer may analyze a tube of a sample and produce a flow cytometry data matrix as an output (e.g., as flow cytometry data). This flow cytometry data matrix may be in, for example, in at least two, three, four, five, six, or seven dimensions. Accordingly, the multidimensional flow cytometry data may comprise one or more of the following: forward scatter (FSC) signals, side scatter (SSC) signals, or fluorescence signals. Characteristics of the signals (e.g., amplitude, frequency, amplitude variations, frequency variations, time dependency, space dependency, etc.) may be treated as dimensions as well. In some embodiments, the fluorescence signals comprise red fluorescence signals, green fluorescence signals, or both. However, any fluorescence signals with other colors may be included in various embodiments.

In certain embodiments, the flow cytometry data matrix may be presented in 2-dimensional matrix form with individual samples for training, validation, or test in columns and features presented in rows. This flow cytometry data matrix may be exported from the flow cytometer in the form of standard format flow cytometry standard (FCS) files.

In various embodiments, automated hematological abnormality detection may involve use of a hematological abnormality classifier to classify multi-dimensional MFC phenotypes as either normal or abnormal. This hematological abnormality classifier may be trained to operate on processed MFC data. This processed MFC data may be data produced by a flow cytometer (e.g., flow cytometry data) that has been processed (e.g., transformed or converted) into a format usable by the hematological abnormality classifier. In various embodiments, the data produced by MFC (e.g., produced by a flow cytometer), or flow cytometry data, may be a flow cytometer data matrix. Also, the processed MFC data may be a high dimensional vector. Furthermore, the hematological abnormality classifier may be trained using a training data set of processed MFC data. This training data set may be based on flow cytometry data (e.g., a flow cytometer data matrix) transformed (e.g., converted) into another data structure (e.g., a high dimensional vector). In some embodiments, the hematological abnormality classifier determines the presence of a hematological abnormality from multi-dimensional MFC phenotypes expressed as high dimensional vectors. Accordingly, the hematological abnormality classifier may be trained using a training data set of multi-dimensional MFC phenotypes expressed as high dimensional vectors. In some embodiments, the training data set is an assembly of high dimensional vectors associated with samples. Also, once trained, the hematological abnormality classifier may be able to classify new processed MFC data (e.g., processed MFC data not within a training data set) as either normal or abnormal (e.g., with a diagnosis of normal or a diagnosis of abnormal).

In certain embodiments, processed MFC data may be data produced by a MFC (e.g., flow cytometry data) that has been processed (e.g., transformed or converted) into a format usable by the hematological abnormality classifier. For example, the flow cytometry data may be a flow cytometer data matrix and the processed MFC data may be a high dimensional vector. This flow cytometer data matrix may be based on recorded raw values from the fluorescent channels (e.g., six fluorescent channels in certain embodiments) of each tube that are max-min normalized. Then, a high dimensional vector may be determined from the flow cytometer data matrix to characterize these raw cell attributes. In certain embodiments, tube high dimensional vectors (e.g., high dimensional vectors associated with respective tubes), may be derived from the flow cytometer data matrix. Accordingly, the original raw cell attributes of each tube of a sample may be expressed as a tube high dimensional vector (e.g., a tube-level feature vector). These tube high dimensional vectors (e.g., vectors of each tube) may formed the final high-dimensional (Dim=2*K*D, where K was the number of Gaussian components and D is the dimension of raw data) input to the hematological abnormality classifier.

Figure 4A:
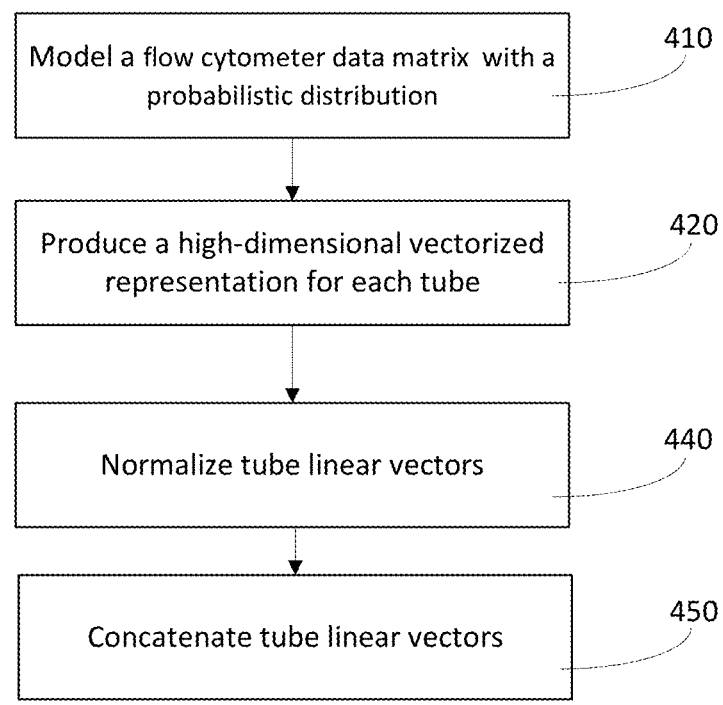
FIG. 4A is a block diagram that illustrates a processed multiparameter flow cytometry (MFC) data production process, in accordance with various embodiments.

FIG. 4A is a block diagram that illustrates a processed multiparameter flow cytometry (MFC) data production process 400, in accordance with various embodiments. The process 400 may be performed at an automated hematological abnormality detection system, as introduced above. The automated hematological abnormality detection system, in some embodiments, comprises at least one of a flow cytometer, a detection server, a datastore, and a user device. In certain embodiments, the automated hematological abnormality detection system may be implemented within a single housing. It is noted that the process 400 is merely an example, and is not intended to limit the present disclosure. Accordingly, it is understood that additional operations (e.g., blocks) may be provided before, during, and after the process 400 of FIG. 4A, certain operations may be omitted, certain operations may be performed concurrently with other operations, and that some other operations may only be briefly described herein.

At block 410, a flow cytometer data matrix expressing each tube's raw attributes values may be modeled with a parametric/non-parametric probabilistic distribution. The probabilistic distribution can be estimated in an optimized mathematical approach to derive the parameters for the distribution.

At block 420, a high-dimensional vectorized representation may be produced by computing a various projection criterions, e.g., differential gradient, maximum posterior adaption, etc. with respect to each or selected subset of the learned probabilistic model parameters learned for each tube of a sample data X.

Accordingly, each tube's projected high dimensional vector (e.g., tube-level feature vector) may be represented as a concatenation of these parameter-specific encoded representation computed with respect to the criterion used.

In certain embodiments, the encoded representation may be produced using a python toolkit. Also, the hyper-parameters used in estimating the parameters of the chosen probability distribution model may be obtained by grid search.

At block 440, each of the tube high dimensional vectors may be normalized. Specifically, the tube high dimensional vectors (e.g., tube-level feature vectors) may be concatenated and normalized to ensure the efficiency in classifier learning. In certain embodiments, the normalization of the vector may be important to ensure that each sample vector (e.g., WC feature vector) is of unit-norm in order to provides better numerical representation that can be used in the hematological abnormality classifier.

At block 450, multiple tube high dimensional vectors (e.g., tube-level vectors) may be concatenated to provide a joint representation of MFC data. Accordingly, each normalized tube high dimensional vectors (e.g., tube-level vectors) for a sample (e.g., a patient) measurement may be concatenated together, to form final feature dimensions. This concatenation of multiple tube high dimensional vectors may be termed as a sample high dimensional vector or a MFC feature vector in certain embodiments. Stated another way, each tube high dimensional vector from the flow cytometer data matrix may represent only a single tube of a sample. These tube high dimensional vectors may be concatenated to produce a sample high dimensional vector (e.g., a MFC feature vector). Accordingly, the initially derived high dimensional vector may be concatenated in a predetermined manner for a consistent phenotype representation across samples to produce a sample high dimensional vector that represents a single sample. Thus, a sample high dimensional vector (e.g., a MFC feature vector) may be determined from the flow cytometer data matrix to characterize raw cell attributes. As noted above, the hematological abnormality classifier may be trained to classify or perform diagnoses on these samples (e.g., as sample high dimensional vectors or MFC feature vectors) as a normal sample or an abnormal sample.

Figure 4B:
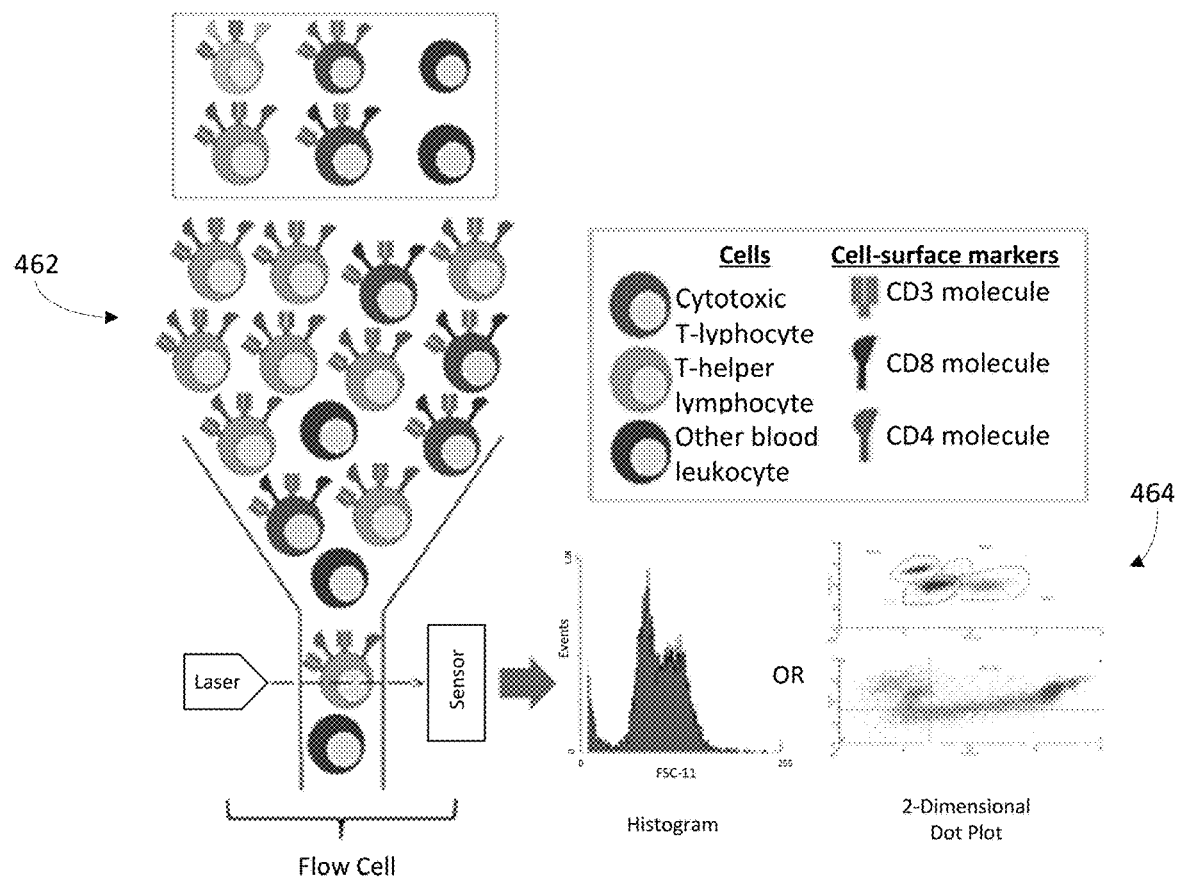
FIG. 4B is an illustrative block diagram of producing data on a tube by tube basis, in accordance with various embodiments.
Figure 4B:
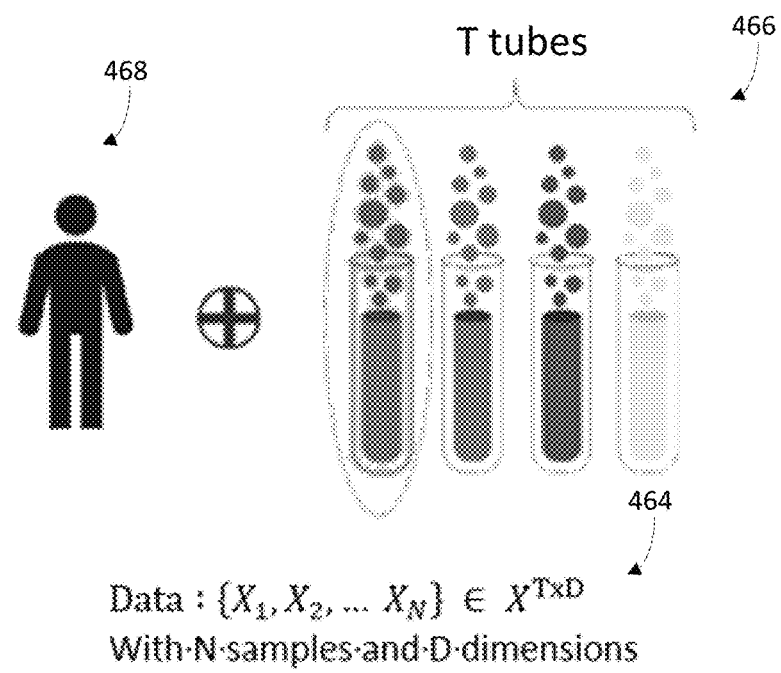

FIG. 4B is an illustrative block diagram of producing data on a tube by tube basis, in accordance with various embodiments. As illustrated in FIG. 4B, MFC 462 may produce MFC data 464 on a tube by tube basis. Each of the tubes 466 may then be represented with their own tube high dimensional vector (e.g., tube level feature vector) and a single sample (e.g., representing a patient 468) may be expressed as multiple tubes 466.

Figure 4C:
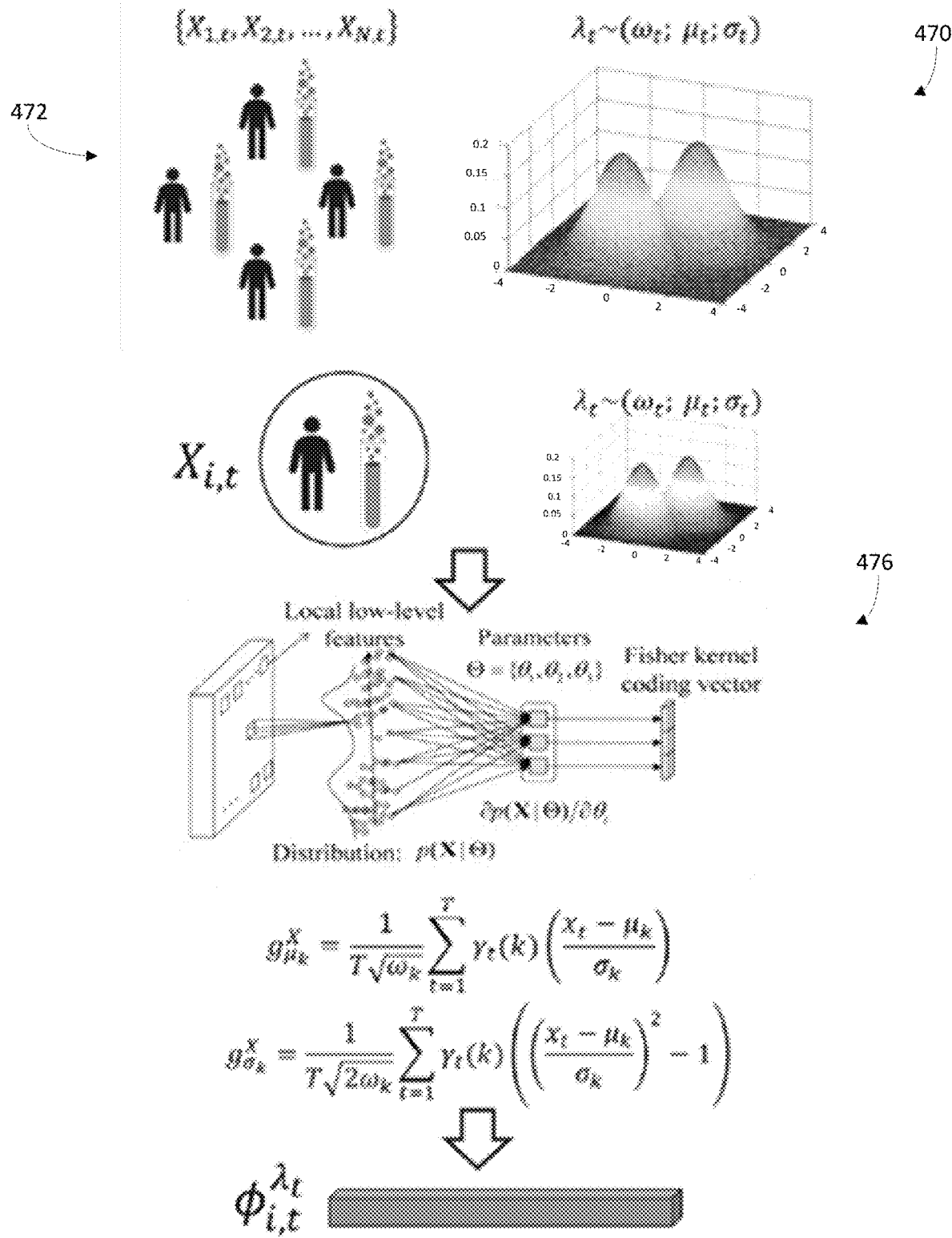
FIG. 4C is an illustrative diagram of producing a tube high dimensional vector, in accordance with various embodiments.

FIG. 4C illustrates an exemplary diagram of producing a high dimensional vector. As illustrated in FIG. 4C, a generative probability distribution 470 may be used to model tubes 472 as a multivariate Gaussian mixture model (GMM). The GMM may be trained in an unsupervised manner using maximum likelihood estimation to derive the model parameters, as noted above. Accordingly, the recorded raw values from the fluorescent channels of each tube 472 may be statistically modeled as a multivariate Gaussian mixture model. The Fisher encoding 476 may be used to derive a high-dimensional vectorized representation (e.g., a tube high dimensional vector 478) by computing the Fisher gradient score with respect to the learned model parameters for each tube sample.

Figure 4D:
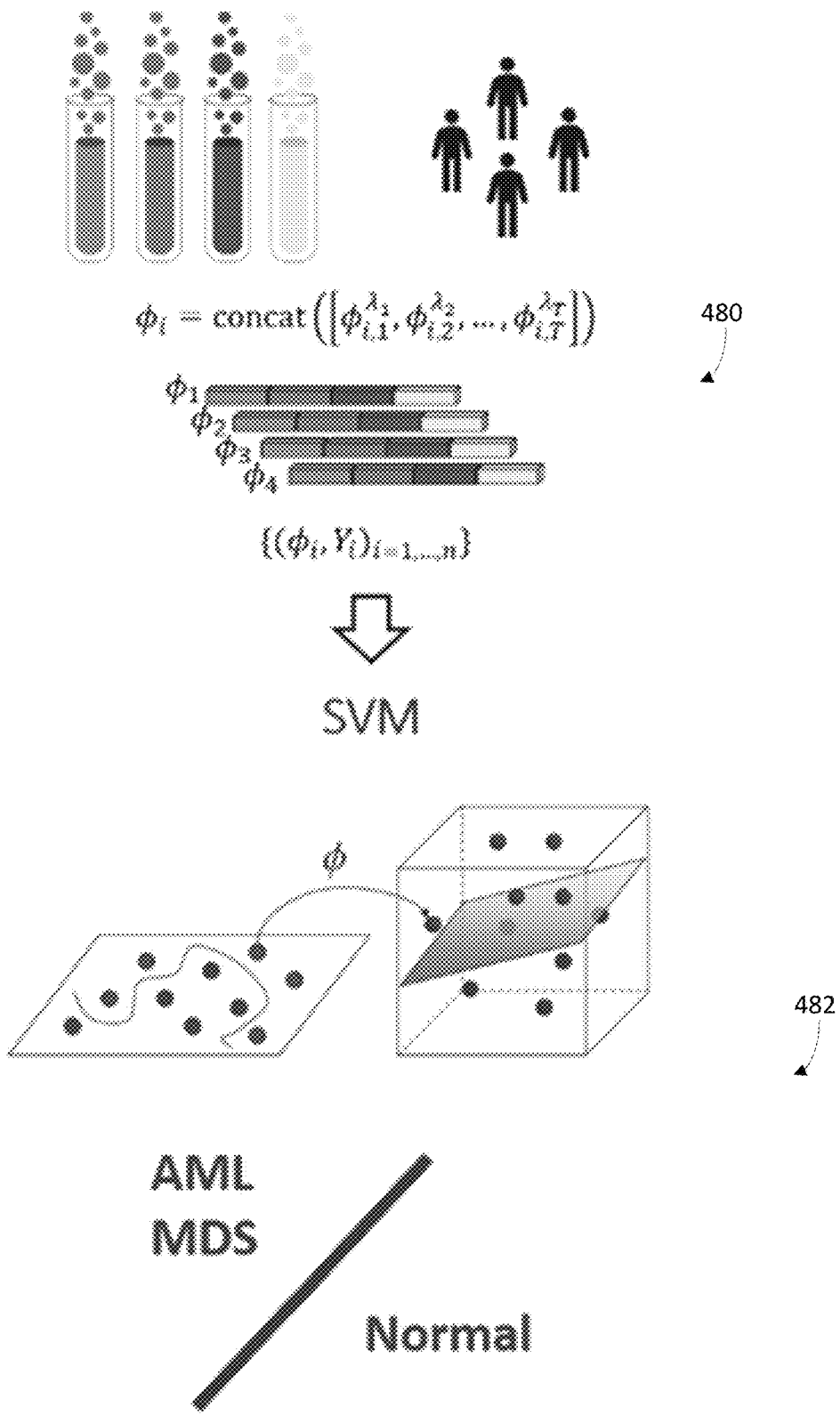
FIG. 4D is an illustrative diagram of concatenation and training, in accordance with various embodiments.

FIG. 4D is an illustrative diagram of concatenation and training, in accordance with various embodiments. As illustrated in FIG. 4D, the concatenation 480 of multiple tube-level vectors provides a joint representation to characterize each sample high dimensional vector (e.g., MFC data, or MFC feature vector). Then, a hematological abnormality classifier may be trained 482 via machine learning (e.g., support vector machines) is to classify the diagnoses (abnormal or normal) on the sample high dimensional vectors.

Diagnostic classification may be performed by a hematological abnormality classifier once the processed MFC data is produced. As noted above, the hematological abnormality classifier may be trained by a supervised machine learning technique such as support vector machine (SVM). Specifically, the hematological abnormality classifier may be trained using a machine learning technique using a training data set based on flow cytometry data (e.g., a flow cytometer data matrix) transformed into a secondary data structure (e.g., a high dimensional vector) and the outcome information (e.g., a known diagnoses of abnormal or normal) associated with each sample of the training data set. Accordingly, this hematological abnormality classifier may represent a supervised machine learning (SML) technique to develop an automated MFC interpretation for detecting MRD objectively in AML and MDS patients. In some embodiments, a linear kernel function may be used with the hematological abnormality classifier, which may be operated by finding a hyper-plane to maximize the classification margin.

Although certain embodiments may describe a particular technique for training a hematological abnormality classifier (e.g., support vector machines (SVM)), the hematological abnormality classifier may be trained using any machine learning technique as desired for different applications in various embodiments. For example, the hematological abnormality classifier may be determined in accordance with any type of machine learning technique to classify the diagnoses (abnormal or normal) of sample high dimensional vectors. These machine learning techniques may be, for example, decision tree learning, association rule learning, artificial neural networks, deep structured learning, inductive logic programming, support vector machines, cluster analysis, Bayesian networks, representation learning, similarity learning, sparse dictionary learning, learning classifier systems, deep learning algorithms, and the like.

Figure 5A:
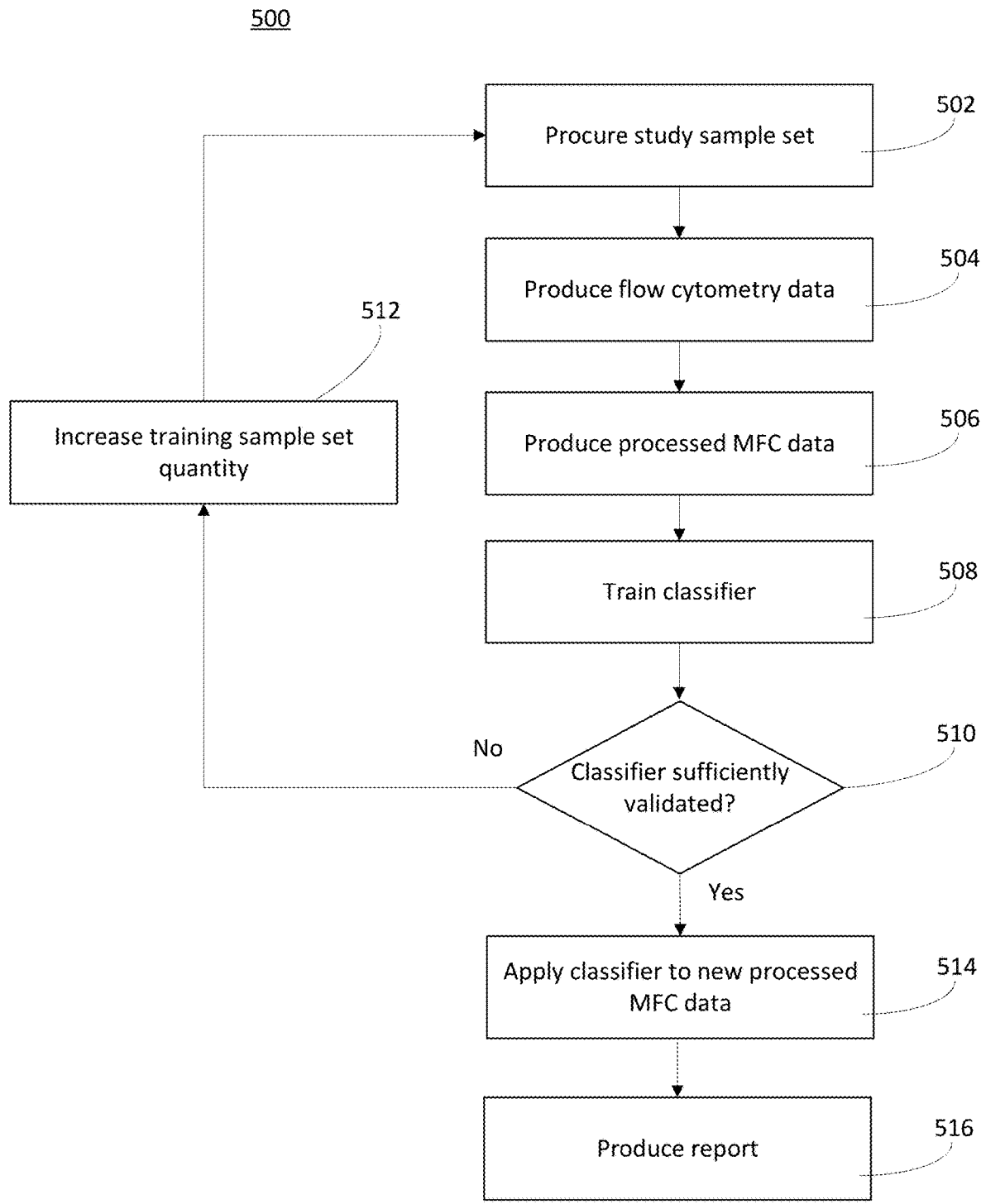
FIG. 5A is a block diagram that illustrates a hematological abnormality classifier process, in accordance with various embodiments.

FIG. 5A is a block diagram that illustrates a hematological abnormality classifier process 500, in accordance with various embodiments. The process 500 may be performed at an automated hematological abnormality detection system, as introduced above. The automated hematological abnormality detection system may include at least one of a flow cytometer, a detection server, a datastore, and a user device. In certain embodiments, the automated hematological abnormality detection system may be implemented within a single housing. It is noted that the process 500 is merely an example, and is not intended to limit the present disclosure. Accordingly, it is understood that additional operations (e.g., blocks) may be provided before, during, and after the process 500 of FIG. 5A, certain operations may be omitted, certain operations may be performed concurrently with other operations, and that some other operations may only be briefly described herein.

At block 502, a study sample set may be collected and processed for input into a flow cytometer. This study sample set may include a training sample set. In certain embodiments, this study sample set may include a validation sample set as well.

The training sample set may be the basis for a training data set utilized for training of the hematological abnormality classifier. Stated another way, the training sample set may be a set of training samples separated into tubes and prepared for input into a flow cytometer. In certain embodiments, a training sample set may include a sufficient number of samples for the hematological abnormality classifier to be sufficiently validated for application of a new data set to classify diagnoses (e.g., abnormal or normal). As will be referenced below, the hematological abnormality classifier may be sufficiently validated when the hematological abnormality classifier achieves at least a threshold amount of accuracy based on the validation sample set. In other embodiments, a training sample set may include any number of samples for the hematological abnormality classifier to be trained so that the hematological abnormality classifier can analyze a new data set to classify diagnoses (e.g., abnormal or normal).

The validation sample set may be the basis of classifier validation (e.g., as referenced in block 510 of process 500). Returning to block 502, more specifically, this validation sample set may be the basis for a validation data set utilized for validation of the hematological abnormality classifier. Stated another way, the validation sample set may be a set of samples separated into tubes and prepared for input into a flow cytometer. In certain embodiments, a validation sample set may include a sufficient number of samples for the hematological abnormality classifier to be validated for application of a new data set to classify diagnoses (e.g., abnormal or normal). As will be referenced below, the hematological abnormality classifier may be sufficiently validated when the hematological abnormality classifier achieves at least a threshold amount of accuracy based on the validation sample set.

In certain embodiments, a study sample set may include from about 1000 to about 2000 or more samples of AML or MDS. Each sample may be associated with a single patient and also be associated as normal or abnormal. Each sample may be represented by multiple tubes (e.g., multiple MFC data points), where each tube may be a discrete input into a flow cytometer. For example, a study sample set of about 1000 to about 2000 samples (e.g., patients) may include a range of about 4000 to about 7000 tubes (e.g., MFC data points). In various embodiments, the tubes (e.g., MFC data points) may also include (e.g., be associated with) post-induction bone marrow MFC data (MFC performed from day+0 to day+45 after the initiation date of induction chemotherapy) and clinical outcomes for survival analysis (e.g., outcome information).

Although specific examples of a study sample set may be described, any study sample set based on a number of samples may be utilized as desired for different applications in various embodiments. For example, in an exemplary embodiment, a study sample set may be part of a study population of 1742 AML or MDS samples (e.g., patients). This number of samples may include total of 5333 tubes (e.g., MFC data points) of bone marrow aspiration. The demographic information of the MFC records enrolled in the study sample set of the exemplary embodiment is illustrated in Table 1:

TABLE 1

Demographic information of MFC records enrolled in the study

| Characteristics | Calibur set, N (%) | Canto-II set, N (%) |
|---|---|---|
| Total MFC record | 2574 (100) | 2759 (100) |
| Total patients | 908 (100) | 1046 (100) |
| Gender (n = 5333) | 2574 (100) | 2759 (100) |
| Female | 1299 (50.5) | 1377 (49.9) |
| Male | 1266 (49.2) | 1374 (49.8) |
| NA | 9 (0.3) | 8 (0.3) |
| Age group (n = 5538) | 2574 (100) | 2759 (10%) |
| <30 | 440 (17.1) | 425 (15.4) |
| 30-39 | 471 (18.3) | 465 (16.9) |
| 40-49 | 436 (16.9) | 507 (18.4) |
| 50-59 | 506 (19.7) | 553 (20.0) |
| >=60 | 697 (27.1) | 790 (28.6) |
| NA | 24 (0.9) | 19 (0.7) |
| Flow Diagnosis (n = 5333) | 2574 (100) | 2759 (100) |
| Acute myeloid leukemia (AML) | 689 (26.8) | 631 (22.9) |
| Myelodysplastic syndrome (MDS) | 137 (5.3) | 226 (8.2) |
| Abnormal (AML + MDS)[a] | 826 (32.1) | 857 (31.1) |
| Normal[b] | 1748 (67.9) | 1902 (68.9) |

Further to Table 1, the term MFC refers to multiparameter flow cytometry. Also, the term NA refers to not applicable.

The term "abnormal" refers to a group that contains samples diagnosed with AML or MDS (e.g., a diagnosis of abnormal). The term "normal" refers to a group that contains both not-malignant or no-MRD MFC data (e.g., a diagnosis of normal). Also, the terms Calibur set and Canto-II set refer to MFC data produced at different respective MFC machines, as will be referenced further below.

In various embodiments, MFC may be performed on bone marrow aspirate samples with a myeloid panel consisting of a set of markers and antibodies. For example, in the exemplary embodiment, a total of 100,000 events were collected for each tube within the panel. Two different flow cytometers may be used in different time periods: 2574 MFC were performed on FASCalibur (Calibur) (Becton Dickinson Bioscience), referencing the Calibur set noted in Table 1, and 2759 MFC on FASCanto-II (Canto-II) (Becton Dickinson Bioscience), referencing the Canto-II set noted in Table 1. Accordingly, reference to Calibur or a Calibur MFC machine may refer to the FASCalibur (Calibur) (Becton Dickinson Bioscience). Also, reference to Canto-II or a Canto-II MFC machine may refer to FASCanto-II (Canto-II) (Becton Dickinson Bioscience).

An exemplary set of markers is provided in Table 2 below:

TABLE 2

Markers measured in each tube within the myeloid panel

| Tube number | 1st | 2nd | 3rd | 4th | 5th | 6th | 7th | 8th | 9th | 10th | 11th | 12th | 13th |
|---|---|---|---|---|---|---|---|---|---|---|---|---|---|
| Channel FITC | N/A | HLA-DR | CD5 | CD56 | CD16 | CD15 | CD14 | CD7 | CD34 | CD2 | HLA-DR | HLA-DR | CD36 |
| PE | N/A | CD11b | CD19 | CD38 | CD13 | CD34 | CD33 | CD56 | CD38 | CD117 | CD34 | CD117 | CD64 |
| PerCP | CD45 | CD45 | CD45 | CD45 | CD45 | CD45 | CD45 | CD45 | CD45 | CD45 | CD45 | CD45 | CD45 |
| APC | N/A | N/A | N/A | N/A | N/A | N/A | N/A | N/A | N/A | N/A | N/A | CD34 | CD34 |

Further to Table 2, markers for each tube may include forward scatter and side scatter taking two channels. Also, the designations of FITC, PE, PercP, and APC refer to fluorophores used in the MFC assay. The designation of "N/A" may refer to having no markers measured in the channel.

Furthermore, an exemplary set of antibodies is provided in Table 3 below:

TABLE 3

Antibodies used in each tube for multicolor flow cytometry analysis.

| Tube | Antibody | Catalog no. | clone | manufacturer | RRID |
|---|---|---|---|---|---|
| 1st | CD45 PerCP | 340665 | 2D1 | BDIS | AB_400075 |
| 2nd | HLA-DR FITC | 340688 | L243 | BDIS | AB_400091 |
| | CD11b PE | 340712 | D12 | BDIS | AB_400112 |
| 3rd | CD5 FITC | 340696 | L17F12 | BDIS | AB_400097 |
| | CD19 PE | 349209 | 4G7 | BDIS | AB_400407 |
| 4th | CD56 FITC | 340723 | NCAM16.2 | BDIS | AB_400121 |
| | CD38 PE | 340676 | HB7 | BDIS | AB_400083 |
| 5th | CD16 FITC | 340704 | NKP15 | BDIS | AB_400104 |
| | CD13 PE | 340686 | L138 | BDIS | AB_400089 |
| 6th | CD15 FITC | IM1423U | 80H5 | Beckman Coulter | AB_131015 |
| | CD34 PE | 340669 | 8G12 | BDIS | AB_400078 |
| 7th | CD14 FITC | 340682 | MφP9 | BDIS | AB_400086 |
| | CD33 PE | 340679 | P67.6 | BDIS | AB_400085 |
| 8th | CD7 FITC | 340738 | M-T701 | BDIS | AB_400124 |
| | CD56 PE | 340724 | NCAM16.2 | BDIS | AB_400122 |
| 9th | CD34 FITC | 340668 | 8G12 | BDIS | AB_400077 |
| | CD38 PE | 340676 | HB7 | BDIS | AB_400083 |
| 10th | CD2 FITC | 340700 | S5.2 | BDIS | AB_400101 |
| | CD117 PE | 340867 | 104D2 | BDIS | AB_400155 |
| 11th | HLA-DR FITC | 340688 | L243 | BDIS | AB_400091 |
| | CD34 PE | 340669 | 8G12 | BDIS | AB_400078 |

TABLE 3-continued

Antibodies used in each tube for multicolor flow cytometry analysis.

| Tube | Antibody | Catalog no. | clone | manufacturer | RRID |
|---|---|---|---|---|---|
| 12th | HLA-DR FITC | 340688 | L243 | BDIS | AB_400091 |
| | CD117 PE | 340867 | 104D2 | BDIS | AB_400155 |
| | CD34 APC | 340667 | 8G12 | BDIS | AB_400531 |
| 13th | CD36 FITC | 555454 | CB38 | BDIS Pharmingen | AB_2291112 |
| | CD64 PE | 644386 | 10.1 | BDIS | AB_1727083 |
| | CD34APC | 340667 | 8G12 | BDIS | AB_400531 |

With respect to cytogenetic and molecular testing, a Trypsin-Giemsa technique may be used for banding metaphase chromosomes. Also, cytogenetic testing may include karyotyping according to the International System for Human Cytogenetic Nomenclature. Genetic mutations including NPM1, FLT3-LTD, CEBPA, RUNX1, and CBFB-MYH11 mutations may be examined. These cytogenetic and genetic mutation analyses conducted at diagnosis may be included for risk stratification, which will be referenced further below.

As noted above, the study sample set may be utilized for training and validation of the hematological abnormality classifier. Accordingly, the sample study set is a set of samples with known outcome information (e.g., a set of outcome labels or an outcome label set characterizing individual outcomes for each of the samples). This known outcome information may be utilized to train the hematological abnormality classifier (e.g., train the hematological abnormality classifier via supervised machine learning based on the known outcome information of the training sample set) and to validate the hematological abnormality classifier (e.g., validate the hematological abnormality classifier via determining the accuracy of the hematological abnormality classifier based on the known outcome information of the training sample set). This outcome information may include labels that indicate whether each sample includes a diagnosis of abnormal or normal For example, with respect to MFC labeling (e.g., production of outcome information), each sample may be manually analyzed using the "different-from-normal" approach introduced above. In certain embodiments, the results may be categorized into 2 main groups, whether normal or abnormal. The abnormal group may include two subgroups: "AML" for freshly diagnosed AML and residual AML cells after treatments, "MDS" for freshly diagnosed MDS and residual MDS cells after treatment. As noted above, the designation of "normal" represents samples without diseased cells (e.g., without abnormality). The labels of normal or abnormal may be mutually exclusive for each sample. Accordingly, each sample may be associated with a discrete label (e.g., normal or abnormal). Also, the collection of these labels may be referred to as outcome information.

In various embodiments, the sample study set may be separated into the training sample set and the validation sample set. This separation may be performed in accordance with principles of cross over validation, where the sample study set is separated into discrete separate portions, with certain portions designated as the training sample set and other portions designated as the validation sample set. For example, the sample study set may be separated into five portions, with four portions utilized as the training sample set and one portion utilized as the validation sample set. Although specific ratios comparing a training sample set and a validation sample set may be described, any ratio comparing a training sample set and a validation sample set may be utilized as desired for different applications in various embodiments. For example, a sample study set may be separated into 2 training sample sets and one validation sample set or 5 training sample sets and two validation sample sets. In particular embodiments, a sample study set may be separated into more training sample sets than validation sample sets. In certain embodiments, a five-fold cross-validation evaluation scheme may be utilized.

In certain embodiments, the study sample set may be further divided to include a prognostic impact sample set, as will be discussed further below. Accordingly, the sample study set may be separated into the training sample set, the validation sample set and (optionally) a prognostic impact sample set. This prognostic impact sample set, may be utilized for further analysis of the long term accuracy of the hematological abnormality classifier (e.g., whether the hematological abnormality classifier not only accurately classified a sample as normal or abnormal, but whether such a classification was ultimately accurate in terms of a health outcome for the patient associated with the sample).

In the exemplary embodiment, the sample study set may be separated into a training sample set, a validation sample set and a prognostic impact sample set. The prognostic impact sample set may include 287 samples and their clinical outcomes for inclusion in a survival analysis. These samples may be of AML patients with available post-induction bone marrow WC data (WC performed from day+0 to day+45 after the initiation date of induction chemotherapy). Their cytogenetic and gene mutation analysis may be used for risk stratification in accordance with the 2017 European LeukemiaNet (ELN) recommendation. Thus, after separating out the prognostic impact sample set of 287 samples, the rest of the study sample set may be 4:1 randomized into the training data set and the validation set, consisting 4039 and 1007 tubes of WC data, respectively.

Thus, in the exemplary embodiment, the 287 post-induction WC data of 287 AML patients may be set aside as a prognostic impact sample set, and the rest of study sample set may be randomly assigned to the training sample set and the validation sample set with 4:1 ratio respectively.

Also, as introduced above for the exemplary embodiment, raw data consisting of a 100,000 (events)*6 (channels) matrix for each tube (as noted in Table 2) together with the flow diagnosis label (e.g., outcome information) in the training sample set may be used to train the hematological abnormality classifier. Accuracy (e.g., for validation) may be determined by comparing the concordance rate between the label (e.g., flow diagnosis label from manually determined outcome information) and determination by the hematological abnormality classifier for each given sample in the validation sample set. As noted above, in certain embodiments, manual analytical results may be blinded to determine labels in outcome information.

As will be referenced below, in the exemplary embodiment, classifiers for pair-wise recognition (AML-vs-normal, MDS-vs-normal and abnormal (AML+MDS)-vs-normal) may be developed independently. In certain embodiments, hematological abnormality classifiers may also be separately developed for MFC data from Calibur and Canto-II, and an independent hematological abnormality classifier may be generated for the combined MFC sub-datasets after conversion of MFC values from Calibur with the conversion formula: Canto-II=Calibur MFI×(218/10,000) provided by the manufacturer.

At block 504, the study sample set may be analyzed using the flow cytometer. As noted above, the flow cytometer may analyze the study sample set on a tube by tube basis. More specifically, the flow cytometer may analyze the study sample set on a tube by tube basis and produce a flow cytometry data matrix as an output (e.g., as flow cytometry data). This flow cytometry data matrix may be in, for example, in at least two, three, four, five, six, or more dimensions. Accordingly, the flow cytometry data may comprise one or more of the following: forward scatter (FSC) signals, side scatter (SSC) signals, or fluorescence signals. Characteristics of the signals (e.g., amplitude, frequency, amplitude variations, frequency variations, time dependency, space dependency, etc.) may be treated as dimensions as well. In some embodiments, the fluorescence signals comprise red fluorescence signals, green fluorescence signals, or both. However, any fluorescence signals with other colors may be included in embodiments.

In certain embodiments, the flow cytometry data matrix may be presented in 2-dimensional matrix form with individual samples for training, validation, or test in columns and features presented in rows. This flow cytometry data matrix may be exported from the flow cytometer in the form of standard format flow cytometry standard (FCS) files.

At block 506, the automated hematological abnormality detection system may produce processed MFC data from the flow cytometry data matrix produced in block 504. As noted above, processed MFC data may be flow cytometry data produced by a MFC that has been processed (e.g., transformed or converted) into a format usable by the hematological abnormality classifier. For example, the flow cytometry data produced by a MFC may be a flow cytometer data matrix and the processed MFC data may be a high dimensional vector. More specifically, a tube high dimensional vector may be derived from the flow cytometer data matrix. Accordingly, the original raw cell attributes of each tube of a sample may be expressed as a tube high dimensional vector (e.g., a tube-level feature vector). These tube high dimensional vectors (e.g., vectors of each tube) may be concatenated to form a final high-dimensional (Dim=2*K*D, where K was the number of Gaussian components and D is the dimension of raw data) input to the hematological abnormality classifier.

In certain embodiments, the processed MFC data may be produced from the flow cytometry data matrix by first expressing each tube's raw attribute values modeled with a generative probability distribution. Specifically, each of the tubes may be statistically-modeled as a multivariate Gaussian mixture model (GMM). Then, a high-dimensional vectorized representation may be produced by computing the Fisher gradient score with respect to the learned model parameters for each tube of a sample. Then, a tube high dimensional vector (e.g., tube-level feature vector) may be derived as the first and second order statistics of the gradient function (e.g., the Fisher gradient). Then, each of the tube high dimensional vectors may be normalized. Lastly, multiple tube high dimensional vectors (e.g., tube-level vectors) may be concatenated to provide a joint representation of MFC data. Accordingly, each normalized tube high dimensional vectors (e.g., tube-level vectors) for a sample (e.g., a patient) measurement may be concatenated together, to form final feature dimensions. This concatenation of multiple tube high dimensional vectors may be termed as a sample high dimensional vector or a MFC feature vector in certain embodiments. The process of producing processed MFC data from the flow cytometry data matrix is discussed in more detail with reference to FIG. 4A, referenced above.

At block 508, the hematological abnormality classifier may be trained based on the processed MFC data associated with the training sample set. As noted above, the hematological abnormality classifier may be trained by a supervised machine learning technique such as support vector machine (SVM). Specifically, the hematological abnormality classifier may be trained using a machine learning technique using a training sample set based on flow cytometry data (e.g., a flow cytometer data matrix) transformed into a secondary data structure (e.g., a high dimensional vector) and the outcome information (e.g., a known diagnoses label of abnormal or normal) associated with each sample of the training data set. Accordingly, this hematological abnormality classifier may represent a supervised machine learning (SML) technique to develop an automated MFC interpretation for detecting MRD objectively in AML and MDS patients.

Although certain embodiments may describe a particular technique for training a hematological abnormality classifier (e.g., support vector machines (SVM)), the hematological abnormality classifier may be trained using any machine learning technique as desired for different applications in various embodiments. For example, the hematological abnormality classifier may be determined in accordance with any type of machine learning technique to classify the diagnoses (abnormal or normal) of sample high dimensional vectors. These machine learning techniques may be, for example, decision tree learning, association rule learning, artificial neural networks, deep structured learning, inductive logic programming, support vector machines, cluster analysis, Bayesian networks, representation learning, similarity learning, sparse dictionary learning, learning classifier systems, and the like.

At block 510, a decision may be made as to whether the hematological abnormality classifier is sufficiently validated. The hematological abnormality classifier may be sufficiently validated when the hematological abnormality classifier achieves at least a threshold amount (e.g., level, percentage, or value) of accuracy based on the validation sample set. As noted above, the study sample set may include a validation sample set as a set of samples that the hematological abnormality classifier may classify (e.g., process) or determine as normal or abnormal. Then, the automated hematological abnormality detection system may compare the hematological abnormality classifier's determination of whether the samples of the validation sample set are normal or abnormal against the known label of normal or abnormal that each sample of the validation sample set is associated with in outcome information. Then, an assessment may be made as to whether the hematological abnormality classifier's determination is sufficiently accurate (e.g., matches with) the known label of normal or abnormal that each sample of the validation sample set is associated with in the outcome information. In certain embodiments, this assessment may be represented with an accuracy value where at least a threshold percentage of the validation sample set is accurately classified (e.g., conforms with) the known label of normal or abnormal in the outcome information. For example, in certain embodiments, the hematological abnormality classifier is sufficiently validated when the accuracy is over 99%, 98%, 97%, 96%, 95%, 94%, 93%, 92%, 91%, 90%, 89%. 88%, 87%, 86%, 85%, 84%, 83%, 82%, 81%, 80% or other readily acceptable percentage acceptable by a skilled person in the art. The process 500 may proceed to block 514 if the hematological abnormality classifier is sufficiently validated (e.g., is at or above a threshold level of accuracy). However, the process 500 may proceed to block 512 if the hematological abnormality classifier is not sufficiently validated (is below or falls below the threshold level of accuracy).

At block 512, the quantity of a training sample set may be increased (e.g., expanded) to further train the hematological abnormality classifier. For example, additional samples may be procured and ascribed to the training sample set so that the study sample set of block 502 (e.g., when repeated) may have more samples in the training sample set than before. Specifically, these additional samples may be utilized to additionally train a previously trained hematological abnormality classifier in block 508 or may be utilized to entirely train a new hematological abnormality classifier starting again from block 502 with an updated study sample set. In further embodiments, a greater proportion of the study sample set may be attributed to the training sample set via an arbitrary setting for the relationship (e.g., a ratio) between the training sample set and other sample sets of the study sample set.

At block 514, the hematological abnormality classifier may be applied to new processed MFC data. This new processed MFC data may be processed MFC data without labels (e.g., without outcome information) and for which new labels are to be ascribed based on the determination of the hematological abnormality classifier. The production of this new processed MFC data is described in greater detail in connection with FIG. 5B.

At block 516, a report may be produced based on the new processed MFC data. This report may be an aggregation of the results (e.g., classifications or determinations) of the new processed MFC data as determined by the hematological abnormality classifier.

Figure 5B:
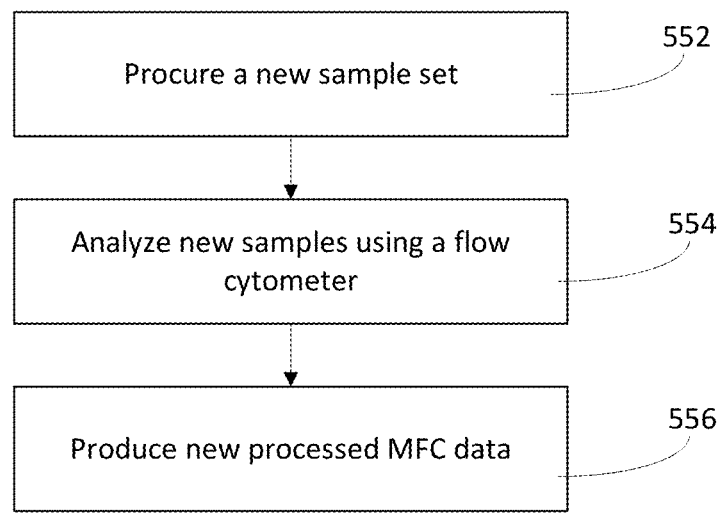
FIG. 5B is a block diagram that illustrates a new processed MFC data production process, in accordance with various embodiments.

FIG. 5B is a block diagram that illustrates a new processed MFC data production process 550, in accordance with various embodiments. The process 550 may be performed at an automated hematological abnormality detection system, as introduced above. The automated hematological abnormality detection system may include at least one of a flow cytometer, a detection server, a datastore, and a user device. In certain embodiments, the automated hematological abnormality detection system may be implemented within a single housing. It is noted that the process 550 is merely an example, and is not intended to limit the present disclosure. Accordingly, it is understood that additional operations (e.g., blocks) may be provided before, during, and after the process 550 of FIG. 5B, certain operations may be omitted, certain operations may be performed concurrently with other operations, and that some other operations may only be briefly described herein.

At block 552, a new sample set may be collected and processed for input into a flow cytometer. This new sample set may include samples that are new (e.g., that do not have labels or outcome information) and to which the hematological abnormality classifier is to produce diagnoses for (e.g., diagnoses of normal or abnormal). Each sample of the new sample set may be associated with a single patient for diagnosis by the hematological abnormality classifier as normal or abnormal. As noted above, a difference between the new sample set and the study sample set is that the study sample set is a set of samples with known outcome information.

Each sample may be represented by multiple tubes (e.g., multiple MFC data points), where each tube may be a discrete input into a flow cytometer. In certain embodiments, these samples of the new sample set may be the same type of sample as that of the study sample set. For example, these samples may be blood, mucus, or bone marrow from a person (e.g., a patient). In preparation for processing by the flow cytometer, the samples may be preprocessed by a immunophenotyping panel consisting of a set of markers and antibodies. An exemplary set of markers is provided in Table 2, noted above. Furthermore, an exemplary set of antibodies is provided in Table 3, noted above.

At block 554, the new sample set may be analyzed using the flow cytometer. As noted above, the flow cytometer may analyze the new sample set on a tube by tube basis. More specifically, the flow cytometer may analyze the new sample set on a tube by tube basis and produce a flow cytometry data matrix as an output. As noted above flow cytometry is a technology for analyzing the physical and chemical characteristics of particles in a fluid that are passed in a stream through a beam of at least one laser. This flow cytometry data matrix may be in, for example, in at least two, three, four, five, six, or more dimensions. Accordingly, the multi-dimensional flow cytometry data may comprise one or more of the following: forward scatter (FSC) signals, side scatter (SSC) signals, or fluorescence signals. Characteristics of the signals (e.g., amplitude, frequency, amplitude variations, frequency variations, time dependency, space dependency, etc.) may be treated as dimensions as well. In some embodiments, the fluorescence signals comprise red fluorescence signals, green fluorescence signals, or both. However, any fluorescence signals with other colors may be included in various embodiments.

In certain embodiments, the flow cytometry data matrix may be presented in 2-dimensional matrix form with individual samples for training, validation, or test in columns and features presented in rows. This flow cytometry data matrix may be exported from the flow cytometer in the form of standard format flow cytometry standard (FCS) files.

At block 556, the automated hematological abnormality detection system may produce new processed MFC data from the flow cytometry data matrix produced in block 554. As noted above, the new processed MFC data may be data produced by a flow cytometer that has been processed (e.g., transformed or converted) into a format usable by the hematological abnormality classifier. For example, the data produced by a MFC may be a flow cytometer data matrix and the processed MFC data may be a high dimensional vector. More specifically, initial high dimensional vectors, also termed as a tube high dimensional vectors, may be derived from the flow cytometer data matrix. Accordingly, the original raw cell attributes of each tube of a sample may be expressed as a tube high dimensional vector (e.g., a tube-level feature vector). These tube high dimensional vectors (e.g., vectors of each tube) may formed the final high-dimensional (Dim=2*K*D, where K was the number of Gaussian components and D is the dimension of raw data) input to the hematological abnormality classifier.

In certain embodiments, the processed MFC data may be produced from the flow cytometry data matrix by first expressing each tube's raw attributes values modeled with a generative probability distribution. Specifically, each of the tubes may be statistically-modeled as a multivariate Gaussian mixture model (GMM). Then, a high-dimensional vectorized representation may be produced by computing the Fisher gradient score with respect to the learned model parameters for each tube of a sample. Then, a tube high dimensional vector (e.g., tube-level feature vector) may be derived as the first and second order statistics of the gradient function (e.g., the Fisher gradient). Then, each of the tube high dimensional vectors may be normalized. Lastly, multiple tube high dimensional vectors (e.g., tube-level vectors) may be concatenated to provide a joint representation of MFC data. Accordingly, each normalized tube high dimensional vectors (e.g., tube-level vectors) for a sample (e.g., a patient) measurement may be concatenated together, to form final feature dimensions. This concatenation of multiple tube high dimensional vectors may be termed as a sample high dimensional vector or a MFC feature vector in certain embodiments. The process of producing processed MFC data from the flow cytometry data matrix is discussed in more detail with reference to FIG. 4, referenced above.

In various embodiments, automated hematological abnormality detection (e.g., via the hematological abnormality classifier) produces a technically desirable practical application. For example, the hematological abnormality classifier has demonstrated a desirable accuracy (ACC) in various embodiments, including the exemplary introduced above and described in greater detail below. This accuracy may be defined as the concordance rate between the diagnoses made manually (e.g., the "difference from normal" approach) and the AI interpretations of the hematological abnormality classifier. Furthermore, the hematological abnormality classifier has also demonstrated a desirable test sensitivity and specificity using area under a receiver operating characteristic (ROC) curve (AUC) in various embodiments, including the exemplary introduced above and described in greater detail below.

A clinical application for MRD detection may include prognostic prediction. The correlation of diagnoses from the hematological abnormality classifier and survival in AML patients may be utilized to demonstrate a clinical application (e.g., via a desirable clinical effectiveness) of the hematological abnormality classifier in detecting MRD. As noted in the exemplary embodiment referenced above, survival analysis was performed on the 287 AML patients in the prognostic impact sample set (e.g., an outcome set), with blinded manual interpretation results at analysis. Overall survival (OS) may be measured from the date of MFC data to the date of allogeneic Hematopoietic Stem Cell Transplant (allo-HSCT), or the date of last follow-up, or death of any cause, whichever comes first. Progression-free survival (PFS) may be measured from the date of MFC data to the date of first relapse, to the date of allo-HSCT, or to the date of last follow-up, whichever comes first. A Kaplan-Meier method may be used to estimate OS and PFS. Cox proportional hazard models may be used to estimate hazard ratios (HRs) for univariate and multivariable analyses of OS and PFS. The hematological abnormality classifier's AI diagnosis of MFC data, genetic risk group, age, gender, and induction chemotherapy may be used as covariates. In certain embodiments, these statistical analyses may be conducted using a survival package in R and Kaplan-Meier curves may be plotted using R.

Accordingly, to evaluate the prognostic significance of the binary classification of the hematological abnormality classifier, a survival analysis may be conducted on 287 AML patients in the prognostic impact sample set (e.g., an outcome set). This survival analysis may include a median follow-up of 21.3 (ranging 1.0-96.1) months. Their demographics of the prognostic impact sample set are illustrated in Table 4:

TABLE 4

Demographics of the prognostic impact sample set

| Sample/Patient characteristics | N (%) |
| --- | --- |
| All samples/patients | 287 (100.0%) |
| Gender (n = 287) | |
| Male | 132 (46.0%) |
| Female | 155 (54.0%) |
| Age (y) (n = 287) | |
| <30 | 21 (7.3%) |
| 30-39 | 61 (21.3%) |
| 40-49 | 57 (19.9%) |
| 50-59 | 63 (22.0%) |
| ≥60 | 85 (29.6%) |
| Induction chemotherapy (n = 287) | |
| Standard | 262 (91.3%) |
| Non-standard | 25 (8.7%) |
| Genetic groups (n = 287) | |
| Adverse | 56 (19.5%) |
| Intermediate | 174 (60.6%) |
| Favorable | 56 (19.5%) |
| NA | 1 (0.3%) |
| HSCT (n = 287) | |
| Yes | 144 (49.8%) |
| No | 143 (50.2%) |

A majority of the patients associated with samples (e.g., 262 patients, or 91.3%) received standard induction chemotherapy. Also, a number of the patients associated with samples (e.g., 144 patients or 49.8%) had received allo-HSCT. A genetic risk stratification may be applied to the prognostic impact sample set with an attribution of adverse, intermediate and favorable risk categories accorded 19.5% (n=56), 60.6% (n=174) and 19.5% (n=56) of the patients, respectively. The patients with abnormal post-induction MFC by the hematological abnormality classifier had significant worse prognosis compared to those with normal one.

Figure 6A:
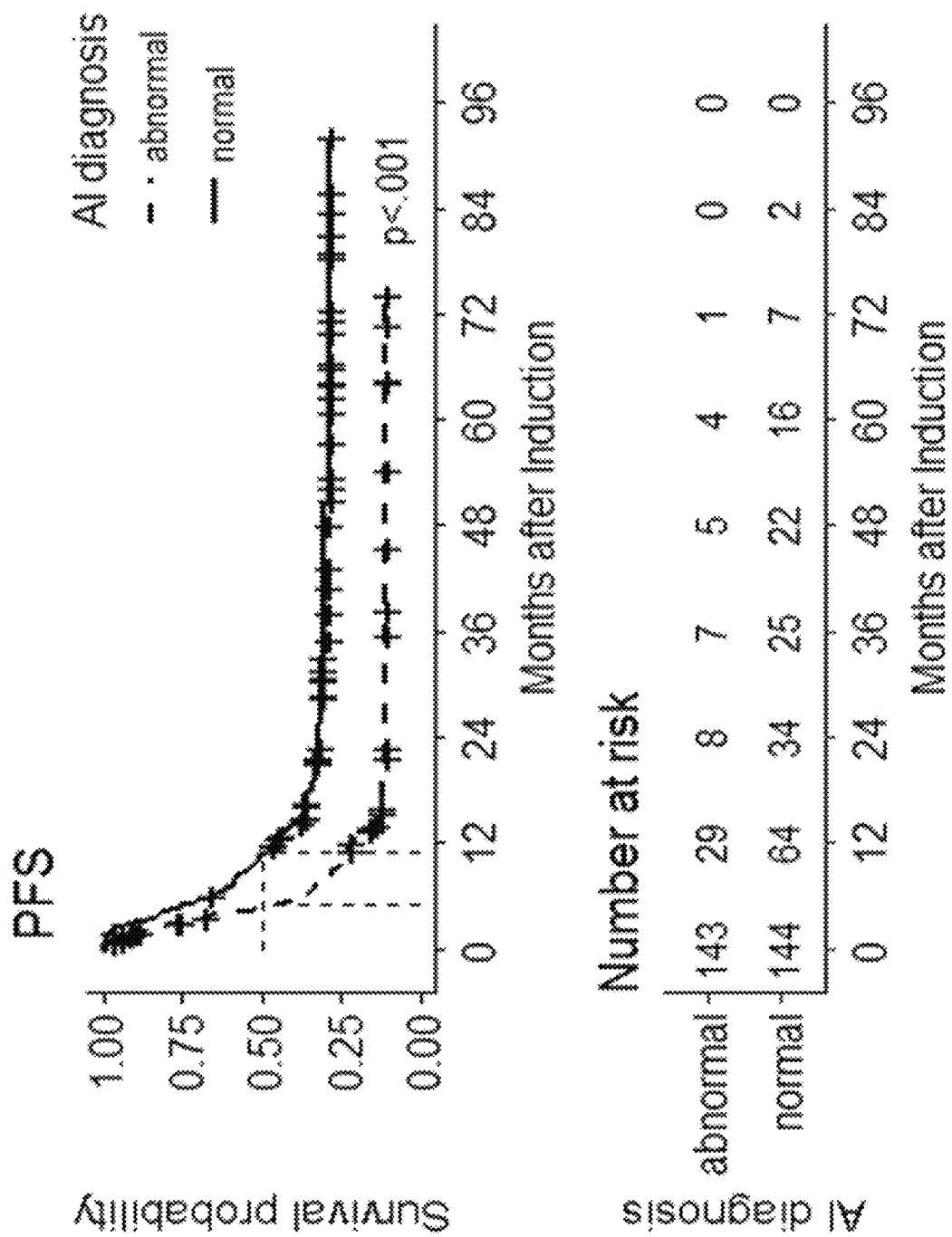
FIG. 6A illustrates various graphs associated with progression-free survival (PFS) in a survival analysis of the prognostic impact sample set, in accordance with various embodiments.
Figure 6B:
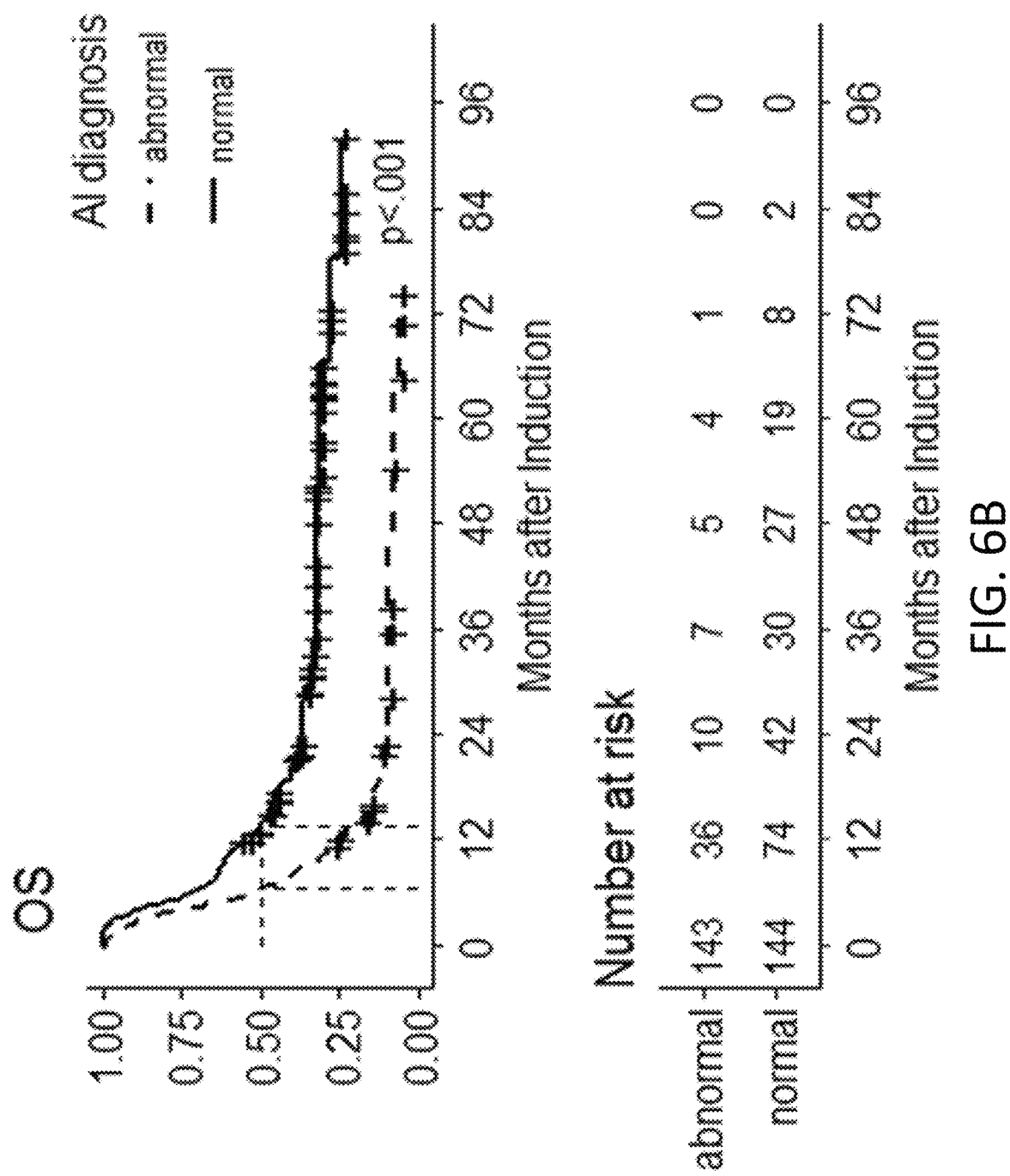
FIG. 6B illustrates various graphs associated with overall survival (OS) in a survival analysis of the prognostic impact sample set, in accordance with various embodiments.

FIGS. 6A and 6B illustrates various Kaplan-Meier curves of progression-free survival (PFS) and overall survival (OS) by post-induction AI diagnosis in patients with AML in the prognostic impact sample set. FIG. 6A illustrates various graphs associated with progression-free survival (PFS) in a survival analysis of the prognostic impact sample set, in accordance with various embodiments. The median PFS is 4.9 (95% confidence interval (CI) 4.4-5.6) vs 10.9 (8.2-14.0) months, with a p value of p<0.0001. Table 5A illustrates the prognostic significance of variables in PFS by univariate and Multivariate Cox proportional hazards regression analysis.

TABLE 5A

Prognostic significance of variables in PFS

| PFS analysis subgroups | Univariate Cox analysis | | Multivariate Cox analysis | |
|---|---|---|---|---|
| | HR (95% CI) | P value | HR (95% CI) | P value |
| Gender (Male:Female) | 1.00 (0.77-1.32) | 0.977 | — | — |
| Age (>50 y: ≤50 y) | 1.19 (0.87-1.63) | 0.288 | — | — |
| Genetic group (favorable:adverse) | 0.27 (0.17-0.42) | <.001 | 0.31 (0.20-0.49) | $3.6 \times 10^{-7}$ |
| Genetic group (intermediate:adverse) | 0.42 (0.30-0.59) | <.001 | 0.42 (0.30-0.59) | $4.9 \times 10^{-7}$ |
| Induction (Standard:non-standard) | 0.63 (0.39-1.01) | 0.057 | — | — |
| AI Diagnosis (no abnormality:abnormal) | 0.48 (0.37-0.63) | <.001 | 0.52 (0.39-0.69) | $4.4 \times 10^{-6}$ |

FIG. 6B illustrates various graphs associated with overall survival (OS) in a survival analysis of the prognostic impact sample set, in accordance with various embodiments. The median OS is 6.5 (95% CI 5.4-8.0) vs 13.6 (11.2-18.8) months, with a p value of p<0.0001. Table 5B illustrates the prognostic significance of variables in OS by univariate and Multivariate Cox proportional hazards regression analysis.

TABLE 5B

Prognostic significance of variables in OS

| OS analysis subgroups | Univariate Cox analysis | | Multivariate Cox analysis | |
|---|---|---|---|---|
| | HR (95% CI) | P value | HR (95% CI) | P value |
| Gender (Male:Female) | 1.02 (0.78-1.33) | 0.885 | — | — |
| Age (>50 y: ≤50 y) | 1.14 (0.84-1.56) | 0.395 | — | — |
| Genetic group (favorable:adverse) | 0.25 (0.16-0.39) | <.001 | 0.31 (0.19-0.48) | $3.8 \times 10^{-7}$ |
| Genetic group (intermediate:adverse) | 0.46 (0.33-0.64) | <.001 | 0.49 (0.35-0.68) | $2.0 \times 10^{-5}$ |
| Induction (Standard:non-standard) | 0.75 (0.44-1.17) | 0.205 | — | — |
| AI Diagnosis (no abnormality:abnormal) | 0.44 (0.34-0.58) | <.001 | 0.51 (0.38-0.67) | $1.4 \times 10^{-6}$ |

As noted in FIGS. 6A, 6B and Tables 5A and 5B, in the univariate analysis, genetic risk groups and MFC diagnosis by the hematological abnormality classifier (e.g., by AI) is impactful in both PFS and OS. Furthermore, this multivariate analysis may confirm genetic risk groups. Lastly, MFC diagnosis by the hematological abnormality classifier (e.g., by AI) may be a prognostic factor.

Furthermore, as noted in FIG. 6A, significant longer post-induction PFS may be observed in the "AI diagnosis: normal" group (median PFS 10.9 months (95% CI 8.2-14.0 months), n=144) compared to the "AI diagnosis: abnormal" group (median PFS 4.9 months (95% CI 4.4-5.6 months), n=143), log-rank P<0.001. Also, as noted in FIG. 6B, significant longer post-induction OS was observed in the "AI diagnosis: normal" group (median OS 13.6 months (95% CI 11.2-18.8 months), n=144) compared to the "AI diagnosis: abnormal" group (median OS 6.5 months (95% CI 5.4-8.0 months), n=143), log-rank P<0.001.

These results were also illustrated by survival curve stratified by genetic risk groups in FIGS. 7A-7F. More specifically, FIGS. 7A-7F illustrate the effect of diagnosis by the hematological abnormality classifier (e.g., by AI) of post-induction MFC on progression-free survival (PFS) and overall survival (OS) in AML patients by 2017 ELN genetic risk groups of the prognostic impact sample set.

Figure 7A:
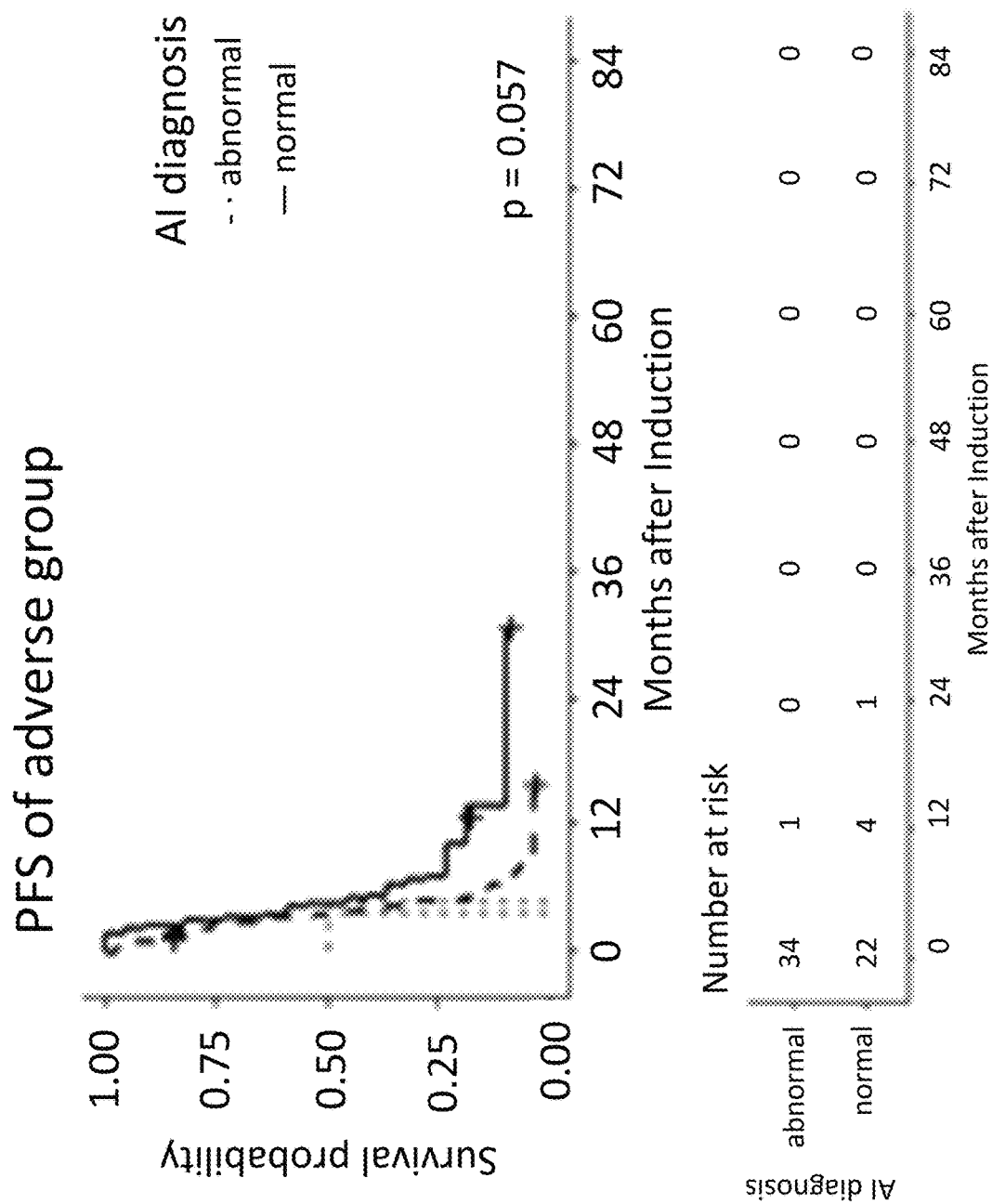
FIG. 7A illustrates a median PFS of hematological abnormality classifier diagnosis abnormal in an adverse risk category group, in accordance with various embodiments.

FIG. 7A illustrates a median PFS of hematological abnormality classifier diagnosis abnormal in an adverse risk category group, in accordance with various embodiments. Specifically, in an adverse risk category group based on the exemplary embodiment, the median PFS of hematological abnormality classifier diagnosis abnormal (n=34) vs normal (n=22) sub-dataset was 3.6 (95% CI 3.4-4.9) vs 4.8 (3.4-7.3) months, P=0.057.

Figure 7B:
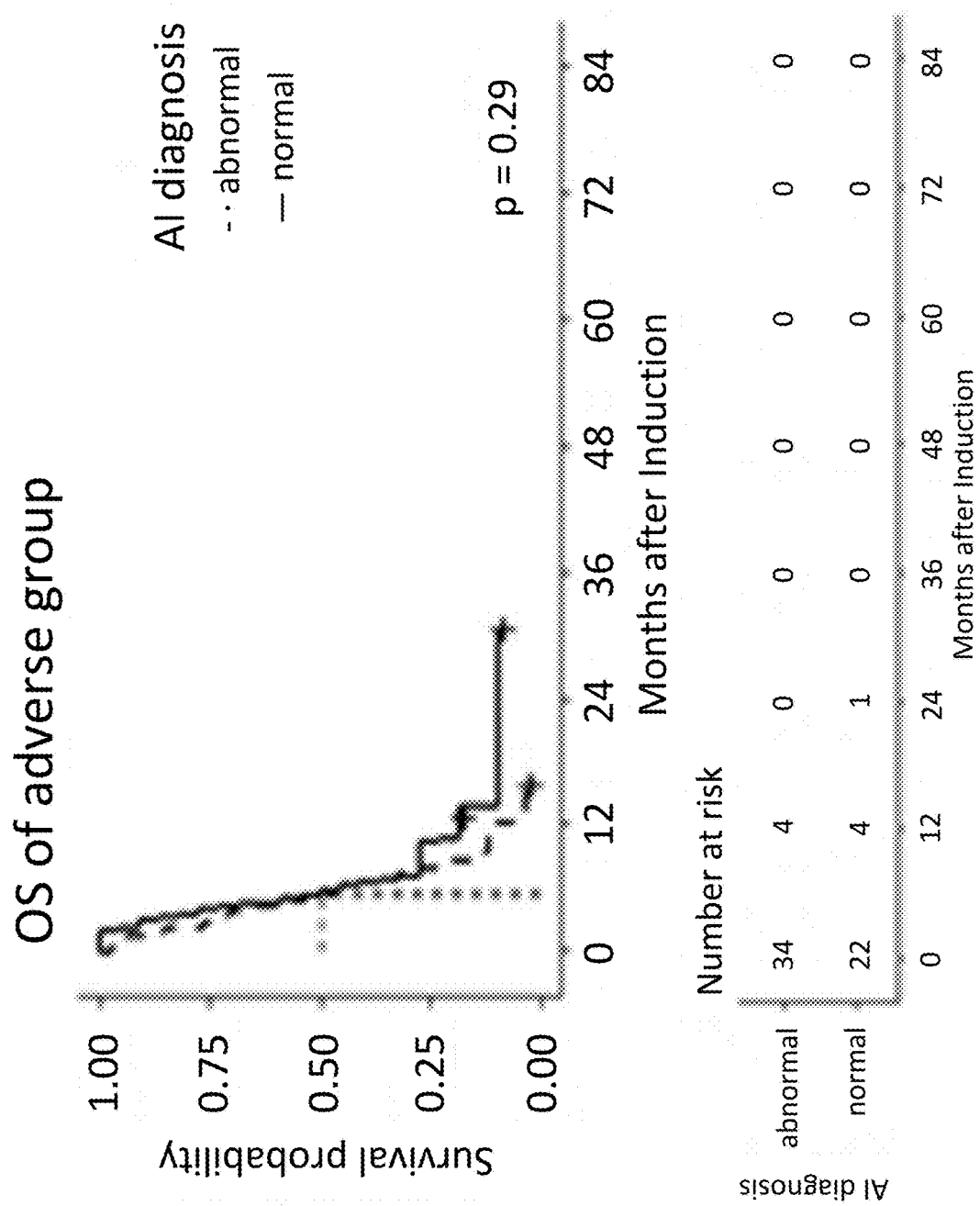
FIG. 7B illustrates a median OS of hematological abnormality classifier diagnosis abnormal in an adverse risk category group, in accordance with various embodiments.

FIG. 7B illustrates a median OS of hematological abnormality classifier diagnosis abnormal in an adverse risk category group, in accordance with various embodiments. Specifically, in an adverse risk category group based on the exemplary embodiment, the median OS of hematological abnormality classifier diagnosis abnormal vs normal sub-dataset was 5.3 (95% CI 4.4-7.6) vs 5.8 (4.7-10.5) months, P=0.29.

Figure 7C:
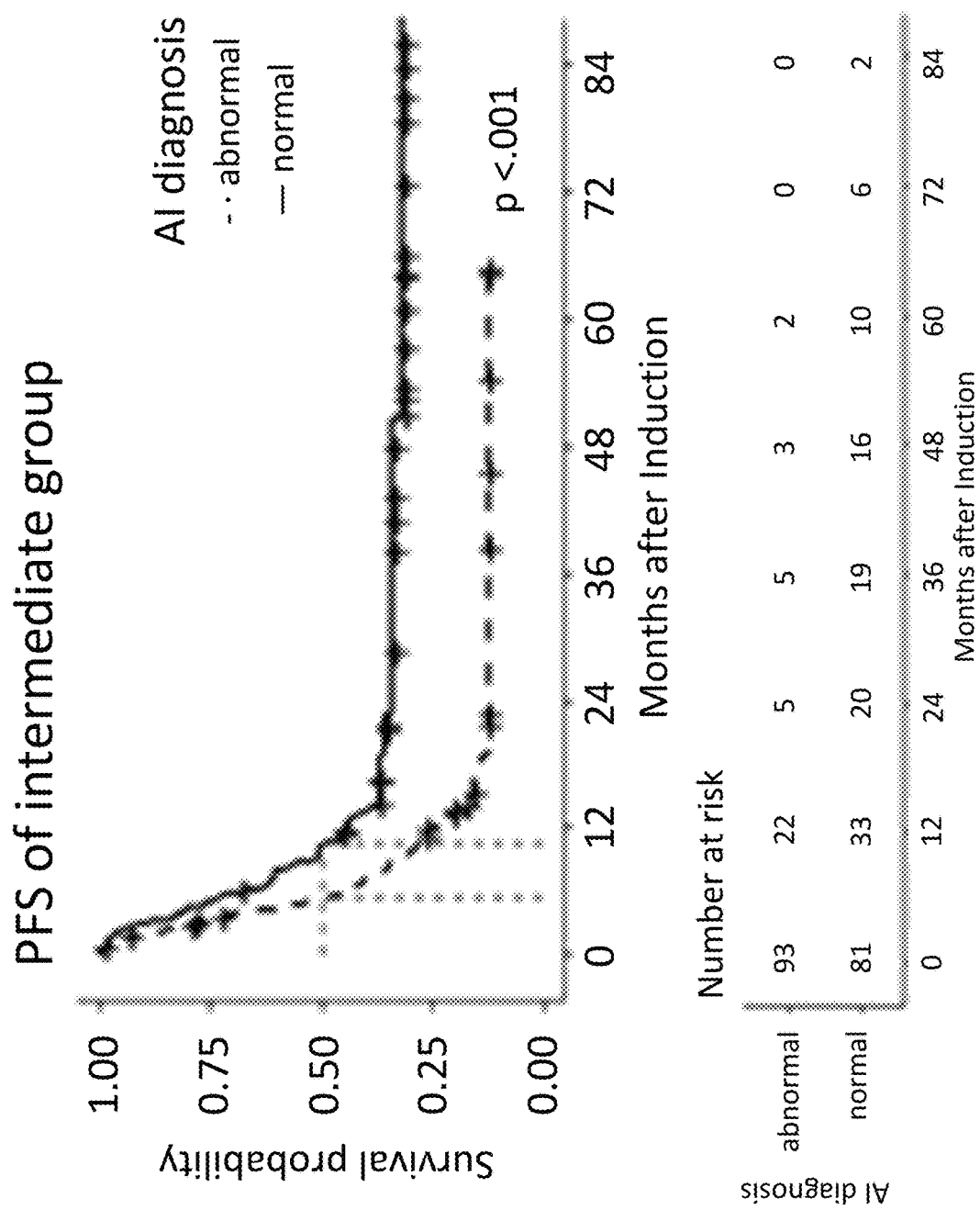
FIG. 7C illustrates a median PFS of hematological abnormality classifier diagnosis abnormal in an intermediate risk category group, in accordance with various embodiments.

FIG. 7C illustrates a median PFS of hematological abnormality classifier diagnosis abnormal in an intermediate risk category group, in accordance with various embodiments. Specifically, in an intermediate risk category group based on the exemplary embodiment, the median PFS of hematological abnormality classifier diagnosis abnormal (n=93) vs normal (n=81) sub-dataset was 5.5 (95% CI 4.5-7.5) vs 10.6 (8.2-14.1) months, P<0.001.

Figure 7D:
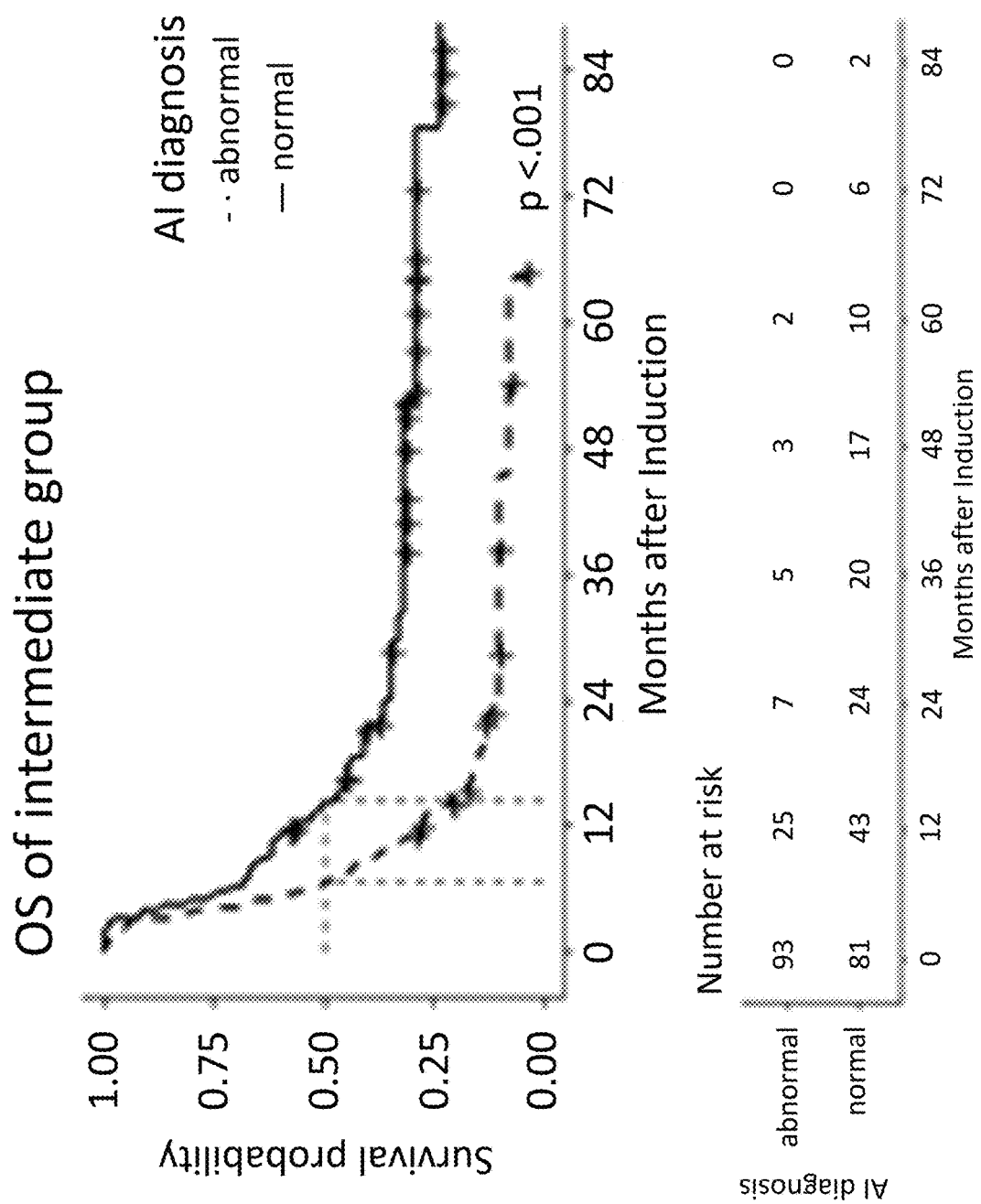
FIG. 7D illustrates a median OS of hematological abnormality classifier diagnosis abnormal in an intermediate risk category group, in accordance with various embodiments.

FIG. 7D illustrates a median OS of hematological abnormality classifier diagnosis abnormal in an intermediate risk category group, in accordance with various embodiments. Specifically, in an intermediate risk category group based on the exemplary embodiment, the median OS of hematological abnormality classifier diagnosis abnormal vs normal sub-dataset was 6.7 (95% CI 5.3-9.1) vs 14.4 (11.2-22.0) months, P<0.001.

Figure 7E:
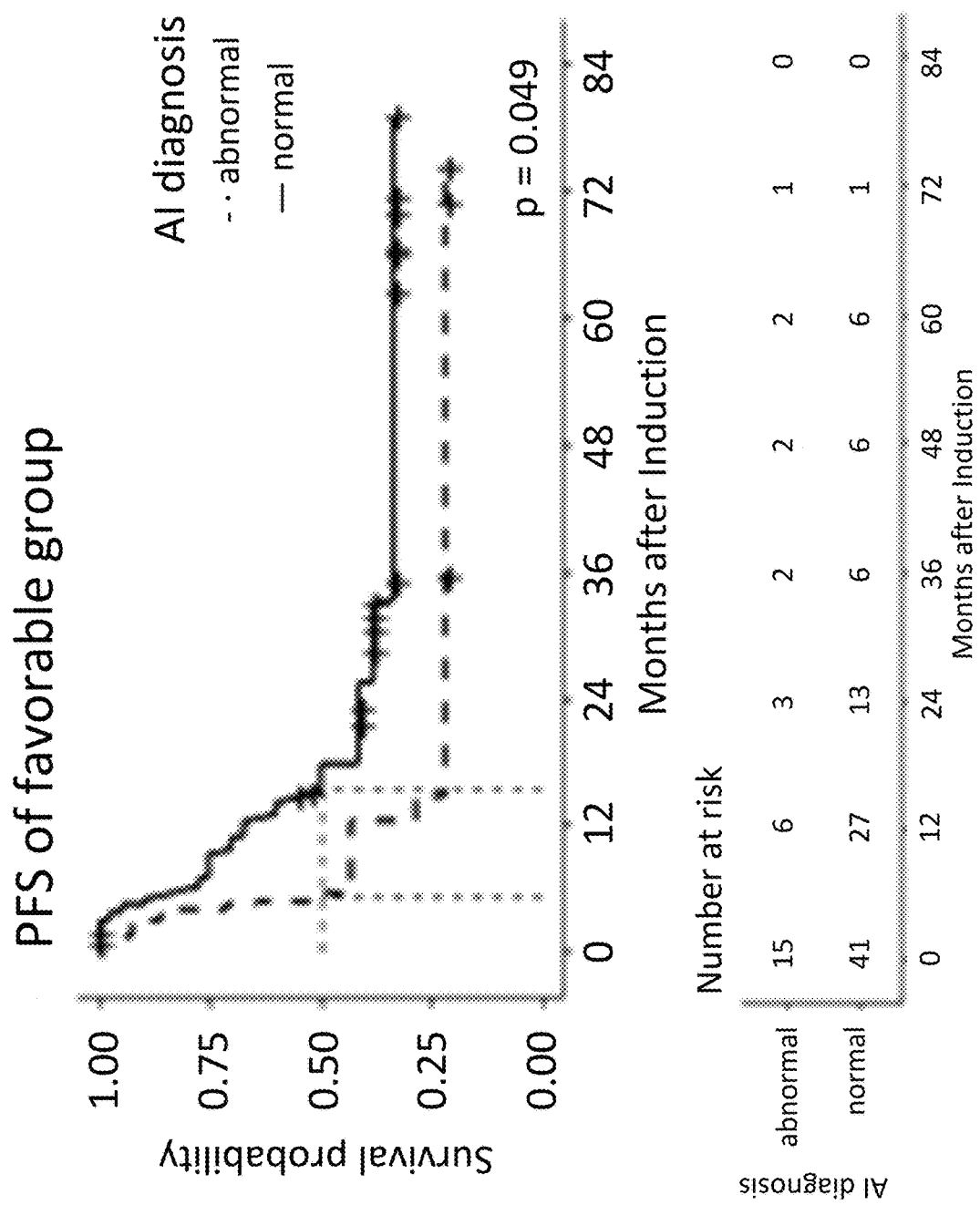
FIG. 7E illustrates a median PFS of hematological abnormality classifier diagnosis abnormal in a favorable risk category group, in accordance with various embodiments.

FIG. 7E illustrates a median PFS of hematological abnormality classifier diagnosis abnormal in a favorable risk category group, in accordance with various embodiments. Specifically, in the favorable risk category group based on the exemplary embodiment, the median PFS of hematological abnormality classifier diagnosis abnormal (n=15) vs normal (n=41) sub-dataset was 5.3 (95% CI 4.8—not reached) vs 15.4 (12.9—not reached) months, P=0.049.

Figure 7F:
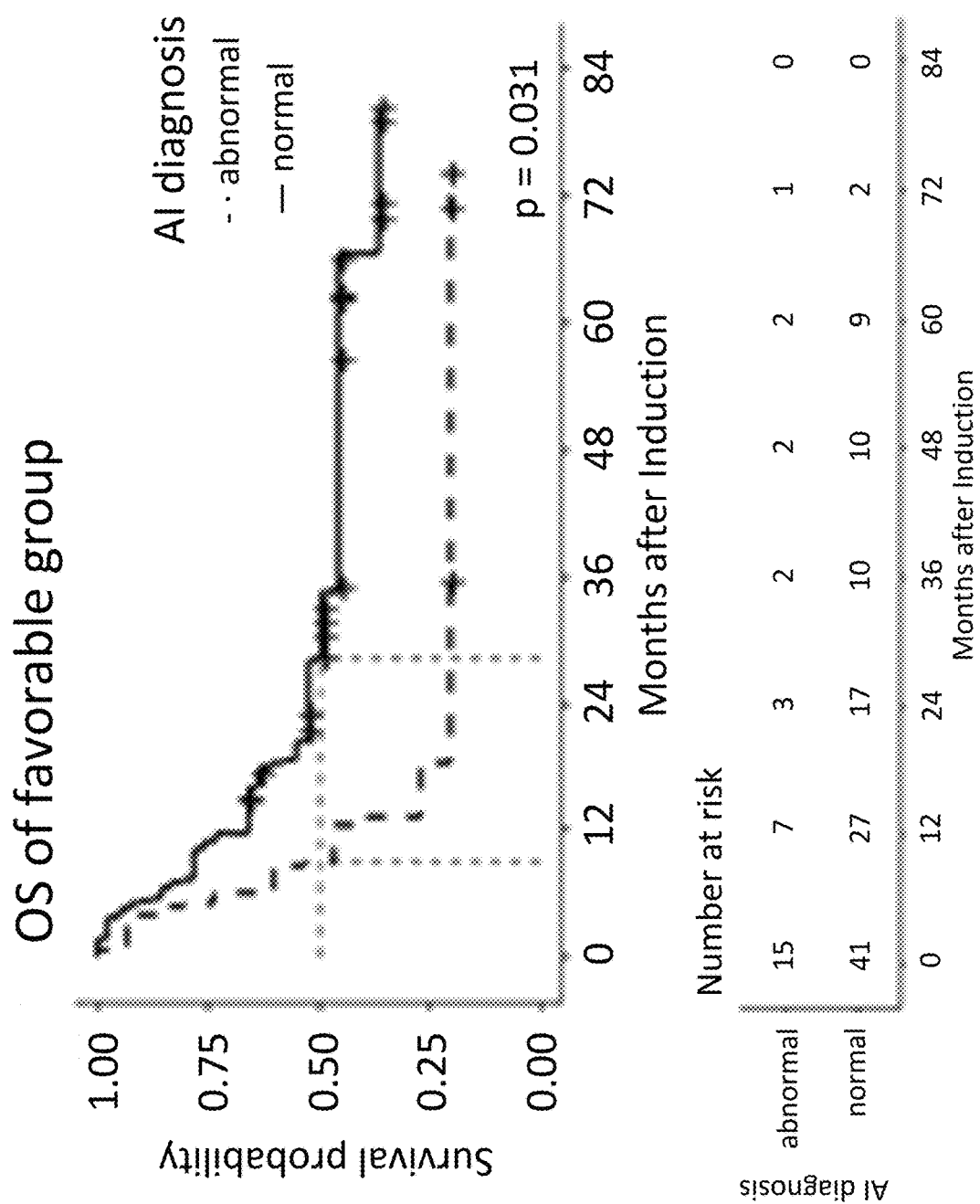
FIG. 7F illustrates a median OS of hematological abnormality classifier diagnosis abnormal in a favorable risk category group, in accordance with various embodiments.

FIG. 7F illustrates a median OS of hematological abnormality classifier diagnosis abnormal in a favorable risk category group, in accordance with various embodiments. Specifically, in the favorable risk category group based on the exemplary embodiment, the median OS of hematological abnormality classifier diagnosis abnormal vs normal sub-dataset was 9.1 (95% CI 6.2—not reached) vs 28.1 (18.0—not reached) months, P=0.031.

Accordingly, for AML patients with favorable genetic risk, those with abnormal post-induction MFC by the hematological abnormality classifier had significant worse PFS and OS than those with normal post-induction MFC (median PFS 5.3 (95% CI 4.8—not reached) vs 15.4 (12.9—not reached) months, p=0.049; median OS 9.1 (95% CI 6.2—not reached) vs 28.1 (18.0—not reached) months, p=0.031). This was also true for AML patients with intermediate genetic risk (median PFS 5.5 (95% CI 4.5-7.5) vs 10.6 (8.2-14.1) months, p<0.001; median OS 6.7 (95% CI 5.3-9.1) vs 14.4 (11.2-22.0) months, p<0.001). However, no significant differences were noted for AML patients with adverse genetic risk.

As noted above, the exemplary embodiment may include the characteristics of 5333 tubes (e.g., MFC data points) of bone marrow aspiration. For Calibur (e.g., the Calibur MFC machine), 2574 tubes (e.g., MFC data points) from 908 samples (e.g., patients) were collected, and 2759 tubes (e.g., MFC data points) from 1046 samples (e.g., patients) for Canto-II (e.g., the Canto-II MFC machine). As much as 31.5% (1683/5333) tubes (e.g., MFC data points) were manually interpreted as abnormal (AML or MDS). Specifically, AML was interpreted in 26.8% of Calibur tubes (e.g., MFC data points) and 22.9% of Canto-II tubes (e.g., MFC data points), and MDS in 5.3% of Calibur tubes (e.g., MFC data points) and 8.2% Canto-II tubes (e.g., MFC data points).

Figure 8A:
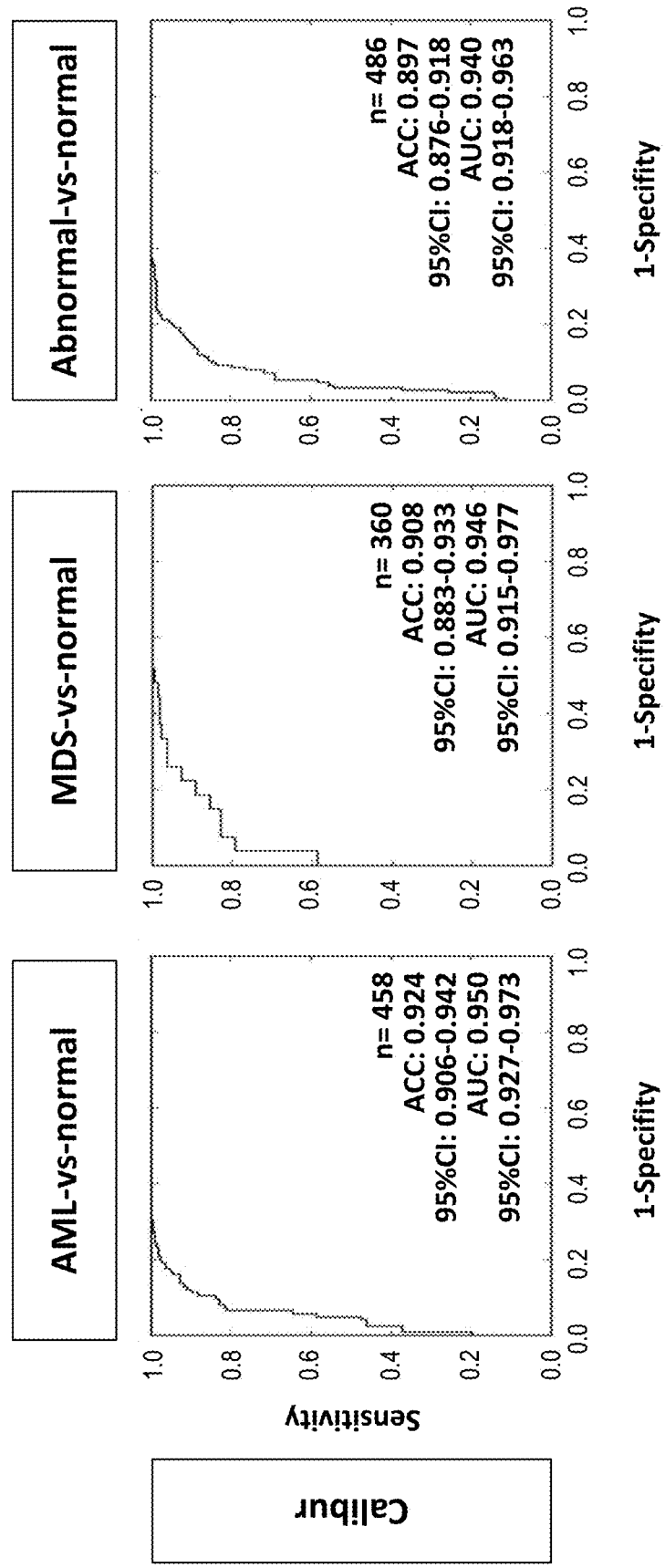
FIG. 8A illustrates performance results for the hematological abnormality classifier in three different comparative scenarios on a Calibur MFC machine, in accordance with various embodiments.
Figure 8B:
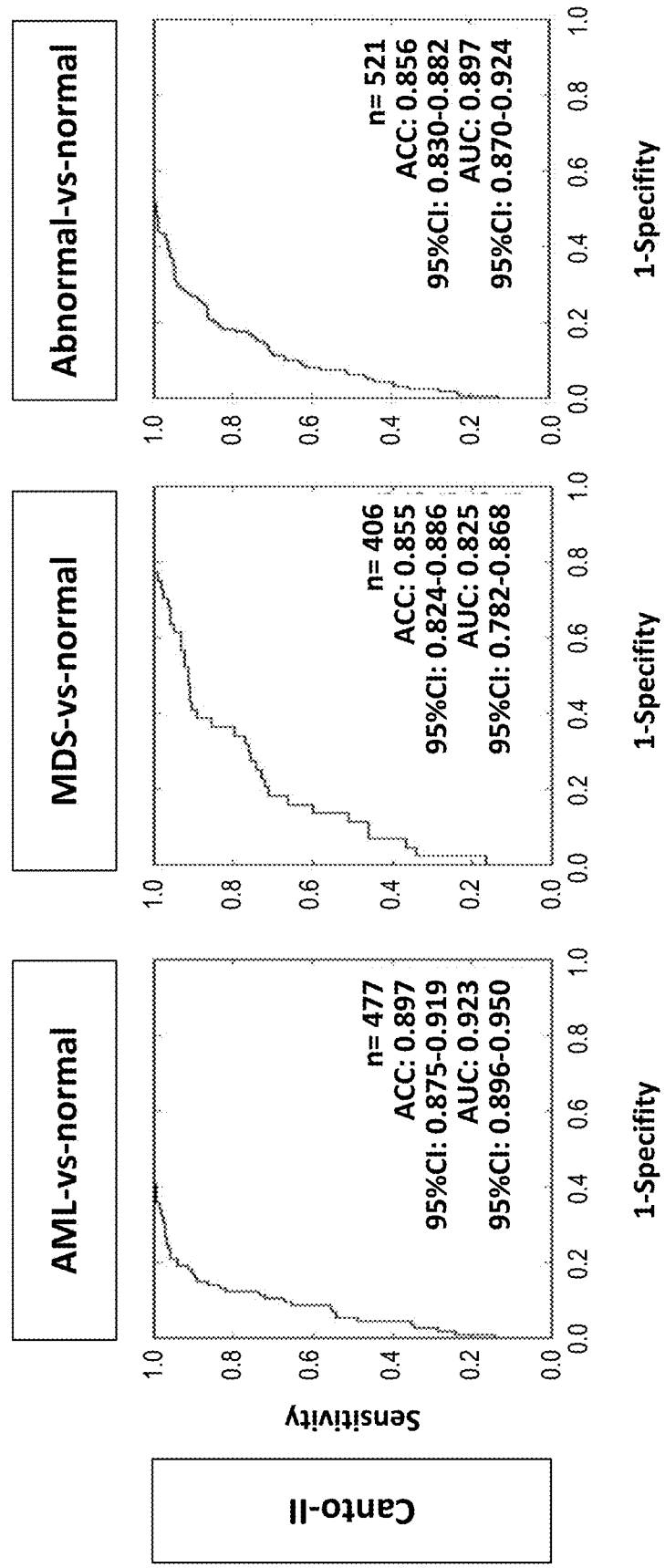
FIG. 8B illustrates performance results for the hematological abnormality classifier in three different comparative scenarios on a Canto-II MFC machine, in accordance with various embodiments.
Figure 8C:
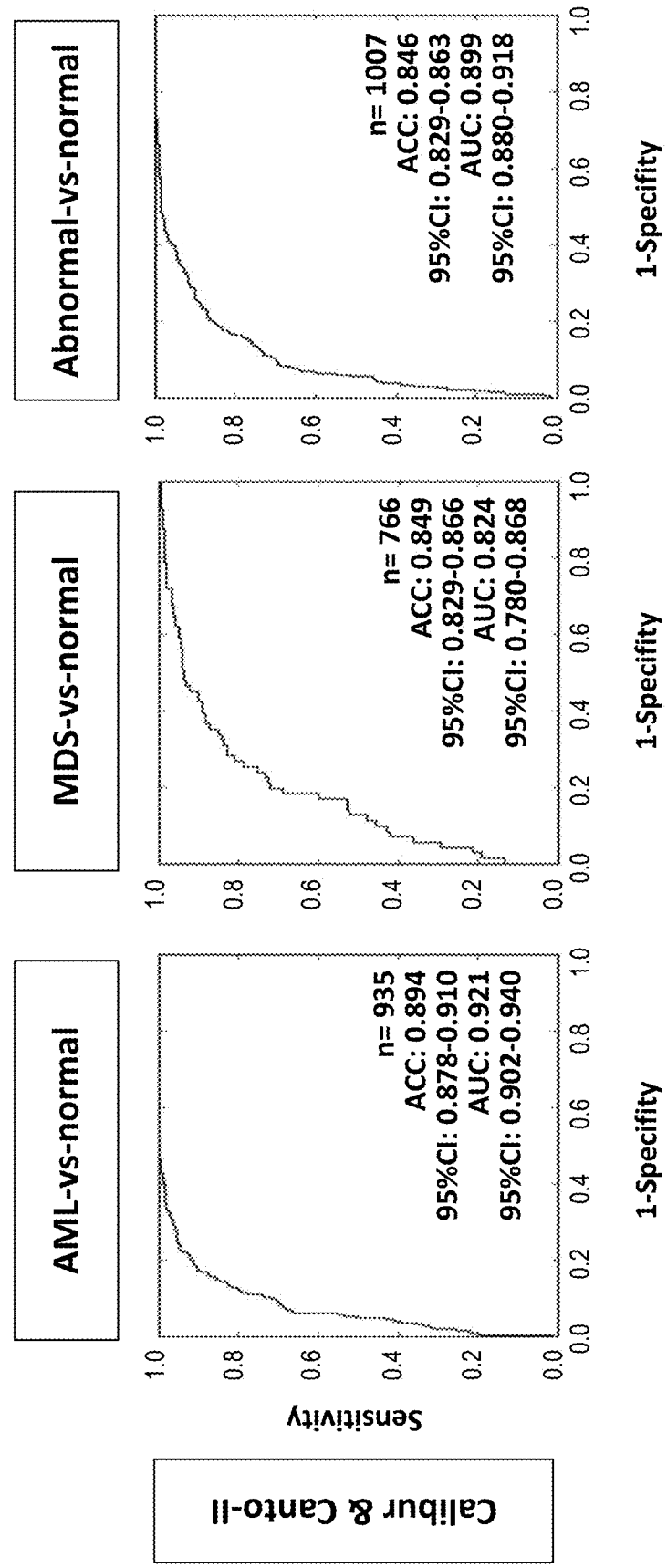
FIG. 8C illustrates performance results for the hematological abnormality classifier in three different comparative scenarios on both the Calibur MFC machine and the Canto-II MFC machine, in accordance with various embodiments.

FIG. 8A illustrates performance results for the hematological abnormality classifier in three different comparative scenarios on a Calibur MFC machine, in accordance with various embodiments. FIG. 8B illustrates performance results for the hematological abnormality classifier in three different comparative scenarios on a Canto-II MFC machine, in accordance with various embodiments. FIG. 8C illustrates performance results for the hematological abnormality classifier in three different comparative scenarios on both the Calibur MFC machine and the Canto-II MFC machine, in accordance with various embodiments. More specifically, FIGS. 8A, 8B, and 8C illustrates various performance results for the hematological abnormality classifier in nine different comparative scenarios: AML-vs-normal, MDS-vs-normal and Abnormal (AML or MDS)-vs-Normal on Calibur, Canto-II, and Calibur+Canto-II, respectively, in accordance with the exemplary embodiment. For reference in view of FIGS. 8A, 8B, and 8C, Table 6 lists out the change in accuracy and AUC as a function of different number of Gaussian components. Both are based on the study sample set of the exemplary embodiment.

In reference to notations in both FIGS. 8A, 8B, and 8C and Table 6, the abnormal group contains samples diagnosed with AML or MDS, the normal group contains both not-malignant or no-MRD MFC data, and K is the number of Gaussian components. Also, the abbreviation "ACC" is for accuracy, the abbreviation "AUC" is for area under the receiver operating characteristic curves, and the abbreviation "CI" is for confidence interval.

As notable in FIGS. 8A, 8B, and 8C, the AML-vs-normal classification accuracy achieved scores ranging from 89.4% to 92.4% in different scenarios, whereas the accuracy of MDS-vs-normal classification achieved 84.9% to 90.8%. For the abnormal-vs-normal classification, the accuracy ranged from 84.6 to 89.7%. Based on the AUC and the shape of ROC curves, the AML-vs-normal classifier had the highest performance, followed by the abnormal-vs-normal and the MDS-vs-normal. Moreover, the overall classifier performance for the Calibur sub-dataset was higher than that for Canto-II sub-dataset, which was relatively equivalent to that for the Calibur+Canto-II sub-dataset.

Table 7 lists out the ACC and AUC for the five-fold cross-validation in the exemplary embodiment:

TABLE 6

Classification performance with different number of Gaussian components

| Abnormal vs normal | Calibur | | | | | |
|---|---|---|---|---|---|---|
|  | K = 4 | | K = 8 | | K = 16 | |
|  | ACC (95% CI) | AUC (95% CI) | ACC (95% CI) | AUC (95% CI) | ACC (95% CI) | AUC (95% CI) |
| Fold 1 | 0.903 (0.881-0.925) | 0.935 (0.913-0.958) | 0.890 (0.867-0.913) | 0.931 (0.907-0.955) | 0.913 (0.892-0.934) | 0.939 (0.916-0.962) |
| Fold 2 | 0.912 (0.891-0.933) | 0.947 (0.927-0.967) | 0.920 (0.900-0.940) | 0.960 (0.945-0.975) | 0.899 (0.878-0.921) | 0.961 (0.947-0.975) |
| Fold 3 | 0.926 (0.906-0.946) | 0.954 (0.936-0.972) | 0.916 (0.894-0.938) | 0.944 (0.923-0.965) | 0.916 (0.895-0.936) | 0.943 (0.922-0.965) |
| Fold 4 | 0.904 (0.881-0.927) | 0.958 (0.942-0.974) | 0.914 (0.892-0.936) | 0.962 (0.947-0.978) | 0.906 (0.884-0.927) | 0.964 (0.947-0.980) |
| Fold 5 | 0.898 (0.874-0.922) | 0.931 (0.908-0.954) | 0.894 (0.870-0.918) | 0.927 (0.902-0.952) | 0.900 (0.877-0.930) | 0.930 (0.907-0.954) |

TABLE 7

Algorithm performance evaluation for each binary classification in five-fold validation

| | | AML vs normal | | | MDS vs normal | | | Abnormal vs normal | | |
|---|---|---|---|---|---|---|---|---|---|---|
| | | N | ACC (95% CI) | AUC (95% CI) | N | ACC (95% CI) | AUC (95% CI) | N | ACC (95% CI) | AUC (95% CI) |
| Calibur | Fold 1 | 458 | 0.924 (0.906-0.942) | 0.950 (0.927-0.973) | 360 | 0.908 (0.883-0.933) | 0.946 (0.915-0.977) | 486 | 0.897 (0.876-0.918) | 0.940 (0.917-0.963) |
| | Fold 2 | 459 | 0.928 (0.908-0.948) | 0.972 (0.958-0.986) | 361 | 0.892 (0.863-0.921) | 0.908 (0.852-0.964) | 486 | 0.899 (0.877-0.921) | 0.958 (0.944-0.972) |
| | Fold 3 | 467 | 0.938 (0.920-0.956) | 0.960 (0.942-0.979) | 365 | 0.926 (0.905-0.947) | 0.950 (0.921-0.978) | 488 | 0.916 (0.896-0.936) | 0.943 (0.922-0.965) |
| | Fold 4 | 443 | 0.935 (0.915-0.955) | 0.940 (0.914-0.965) | 354 | 0.890 (0.865-0.915) | 0.947 (0.919-0.974) | 488 | 0.906 (0.884-0.928) | 0.964 (0.947-0.980) |
| | Fold 5 | 465 | 0.925 (0.906-0.944) | 0.961 (0.940-0.982) | 365 | 0.885 (0.858-0.912) | 0.923 (0.891-0.955) | 482 | 0.900 (0.877-0.923) | 0.930 (0.907-0.954) |
| Canto-II | Fold 1 | 477 | 0.897 (0.875-0.919) | 0.923 (0.896-0.950) | 406 | 0.855 (0.824-0.886) | 0.825 (0.782-0.868) | 521 | 0.856 (0.830-0.882) | 0.897 (0.878-0.916) |
| | Fold 2 | 477 | 0.889 (0.867-0.911) | 0.910 (0.878-0.942) | 406 | 0.796 (0.770-0.822) | 0.899 (0.858-0.940) | 521 | 0.871 (0.849-0.893) | 0.900 (0.886-0.914) |
| | Fold 3 | 466 | 0.893 (0.869-0.917) | 0.926 (0.899-0.953) | 402 | 0.823 (0.792-0.854) | 0.808 (0.749-0.867) | 522 | 0.835 (0.808-0.862) | 0.892 (0.867-0.917) |
| | Fold 4 | 475 | 0.888 (0.864-0.912) | 0.903 (0.871-0.935) | 408 | 0.814 (0.782-0.846) | 0.853 (0.798-0.908) | 518 | 0.842 (0.816-0.868) | 0.848 (0.811-0.885) |
| | Fold 5 | 489 | 0.883 (0.858-0.908) | 0.921 (0.891-0.950) | 407 | 0.887 (0.861-0.913) | 0.878 (0.826-0.930) | 523 | 0.857 (0.832-0.882) | 0.903 (0.877-0.929) |
| Calibur & Canto-II | Fold 1 | 933 | 0.894 (0.878-0.910) | 0.921 (0.902-0.940) | 764 | 0.849 (0.829-0.869) | 0.824 (0.780-0.868) | 1004 | 0.846 (0.829-0.863) | 0.899 (0.880-0.918) |
| | Fold 2 | 934 | 0.908 (0.892-0.924) | 0.937 (0.919-0.955) | 765 | 0.873 (0.851-0.895) | 0.890 (0.855-0.925) | 1005 | 0.873 (0.856-0.890) | 0.915 (0.897-0.933) |
| | Fold 3 | 933 | 0.899 (0.882-0.916) | 0.921 (0.901-0.941) | 767 | 0.854 (0.833-0.875) | 0.822 (0.774-0.870) | 1010 | 0.862 (0.844-0.880) | 0.888 (0.866-0.910) |
| | Fold 4 | 940 | 0.894 (0.878-0.910) | 0.909 (0.887-0.931) | 762 | 0.814 (0.791-0.837) | 0.868 (0.827-0.908) | 1006 | 0.851 (0.833-0.869) | 0.887 (0.866-0.909) |
| | Fold 5 | 933 | 0.892 (0.874-0.910) | 0.908 (0.886-0.930) | 773 | 0.885 (0.866-0.904) | 0.879 (0.840-0.917) | 1006 | 0.853 (0.835-0.871) | 0.888 (0.867-0.909) |

In reference to notations in Table 7, the abnormal group contains samples diagnosed with AML or MDS, and the normal group contains both not-malignant or no-MRD MFC data. Also, the abbreviation "ACC" is for accuracy of the concordance rate with the flow diagnosis of MFC records in the validation set, the abbreviation "AUC" is for area under the receiver operating characteristic curves, and the abbreviation "CI" is for confidence interval. The "N" value indicates the number of MFC data in the analysis for each column. Accordingly, Table 7 illustrates binary classification performance for the AML-vs-normal, MDS-vs-normal and abnormal-vs-normal groups: (A) Calibur sub-dataset, (B) Canto-II sub-dataset, (C) Calibur & Canto-II sub-dataset.

A feature selection analysis may be performed to find the relative importance of markers in the hematological abnormality classifier. This feature selection analysis may be performed based on the exemplary embodiment. In a first round, the hematological abnormality classifier is trained with data from just one tube to determine the best tube with the highest AUC. The abnormal-vs-normal comparison may be used for analysis for Calibur and Canto-II, with two-fold cross-validation. This single tube feature selection analysis with two-fold validation is illustrated in Table 8:

TABLE 8

Single tube feature selection analysis with two-fold validation

| | | AUC of each individual tube | | | | | | |
|---|---|---|---|---|---|---|---|---|
| Datasets | | 1st | 2nd | 3rd | 4th | 5th | 6th | 7th |
| Calibur | Fold 1 | 0.898 | 0.924 | 0.913 | 0.917 | 0.902 | 0.917 | 0.914 |
| | N | 2014 | 2016 | 2016 | 2016 | 2011 | 2011 | 2010 |
| | Fold 2 | 0.920 | 0.932 | 0.928 | 0.934 | 0.933 | 0.931 | 0.943 |
| | N | 2070 | 2071 | 2072 | 2072 | 2068 | 2069 | 2069 |
| Canto-II | Fold 1 | 0.829 | 0.840 | 0.850 | 0.844 | 0.847 | 0.857 | 0.844 |
| | N | 2149 | 2150 | 2149 | 2150 | 2149 | 2149 | 2149 |
| | Fold 2 | 0.843 | 0.848 | 0.849 | 0.858 | 0.869 | 0.859 | 0.859 |
| | N | 2197 | 2197 | 2196 | 2197 | 2196 | 2196 | 2196 |

TABLE 8-continued

Single tube feature selection analysis with two-fold validation

| Datasets | | 8th | 9th | 10th | 11th | 12$^{th}$ | 13th |
|---|---|---|---|---|---|---|---|
| | | AUC of each individual tube | | | | | |
| Calibur | Fold 1 | 0.911 | 0.931 | 0.931 | 0.924 | — | — |
| | N | 2010 | 1876 | 1908 | 2012 | — | — |
| | Fold 2 | 0.939 | 0.937 | 0.940 | 0.934 | | |
| | N | 2069 | 1927 | 1964 | 2070 | | |
| Canto-II | Fold 1 | 0.832 | 0.870 | 0.863 | 0.860 | 0.841 | 0.841 |
| | N | 2149 | 2147 | 1386 | 1290 | 798 | 815 |
| | Fold 2 | 0.821 | 0.874 | 0.858 | 0.841 | 0.844 | 0.886 |
| | N | 2196 | 2193 | 1424 | 1322 | 816 | 828 |

The markers measured in each tube are the same as that noted in Table 2, above. As shown in Table 8, learning from one single tube could yield a reliable AUC (ranging from 0.898 to 0.943 for Calibur, and from 0.829 and 0.886 for Canto-II). However, the tubes with the best performance may not be the same for both Calibur and Canto-II (e.g., the 5th tube (CD16/CD13/CD45) for Calibur and 2nd tube (HLA-DR/CD11b/CD45) for Canto-II).

The hematological abnormality classifier may be further trained by adding data from each of the remained tubes to that from previous selected tube(s). Based on this training, the best 2-tube combination with highest AUC may be found and the process may be repeated until data from all tubes are included. Table 9 details this single tube feature selection analysis with two-fold validation:

TABLE 9

Tubes included in feature selection analysis.

| AML Panel | | Calibur-fold1 | | | Calibur-fold2 | | |
|---|---|---|---|---|---|---|---|
| | | AUC | Tubes included | N | AUC | Tubes included | N |
| Number of tubes included | 1 | 0.924 | 5$^{th}$ | 2017 | 0.945 | 5$^{th}$ | 2069 |
| | 2 | 0.925 | 5$^{th}$, 11$^{th}$ | 2016 | 0.948 | 5$^{th}$, 11$^{th}$ | 2069 |
| | 3 | 0.928 | 5$^{th}$, 9$^{th}$, 11$^{th}$ | 2017 | 0.947 | 3$^{rd}$, 5$^{th}$, 11$^{th}$ | 2069 |
| | 4 | 0.922 | 2$^{nd}$, 5$^{th}$, 9$^{th}$, 11$^{th}$ | 2017 | 0.943 | 3$^{rd}$, 5$^{th}$, 9$^{th}$, 11$^{th}$ | 2070 |
| | 5 | 0.930 | 2$^{nd}$, 4$^{th}$, 5$^{th}$, 9$^{th}$, 11$^{th}$ | 2017 | 0.944 | 2$^{nd}$, 3$^{rd}$, 5$^{th}$, 9$^{th}$, 11$^{th}$ | 2070 |
| | 6 | 0.930 | 2$^{nd}$, 4$^{th}$, 5$^{th}$, 9$^{th}$, 10$^{th}$, 11$^{th}$ | 2017 | 0.947 | 2$^{nd}$, 3$^{rd}$, 5$^{th}$, 9$^{th}$, 10$^{th}$, 11$^{th}$ | 2070 |
| | 7 | 0.924 | 2$^{nd}$, 3$^{rd}$, 4$^{th}$, 5$^{th}$, 9$^{th}$, 10$^{th}$, 11$^{th}$ | 2017 | 0.947 | 2$^{nd}$, 3$^{rd}$, 5$^{th}$, 8$^{th}$, 9$^{th}$, 10$^{th}$, 11$^{th}$ | 2070 |
| | 8 | 0.922 | 2$^{nd}$, 3$^{rd}$, 4$^{th}$, 5$^{th}$, 6$^{th}$, 9$^{th}$, 10$^{th}$, 11$^{th}$ | 2017 | 0.945 | 2$^{nd}$, 3$^{rd}$, 4$^{th}$, 5$^{th}$, 8$^{th}$, 9$^{th}$, 10$^{th}$, 11$^{th}$ | 2070 |
| | 9 | 0.922 | 2$^{nd}$, 3$^{rd}$, 4$^{th}$, 5$^{th}$, 6$^{th}$, 8$^{th}$, 9$^{th}$, 10$^{th}$, 11$^{th}$ | 2013 | 0.950 | 2$^{nd}$, 3$^{rd}$, 4$^{th}$, 5$^{th}$, 7$^{th}$, 8$^{th}$, 9$^{th}$, 10$^{th}$, 11$^{th}$ | 2071 |
| | 10 | 0.922 | 1$^{st}$, 2$^{nd}$, 3$^{rd}$, 4$^{th}$, 5$^{th}$, 6$^{th}$, 8$^{th}$, 9$^{th}$, 10$^{th}$, 11$^{th}$ | 2012 | 0.948 | 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ | 2069 |
| | 11 | 0.900 | 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ | 2011 | 0.933 | 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ | 2068 |

| AML Panel | | CantoII-fold1 | | | CantoII-fold2 | | |
|---|---|---|---|---|---|---|---|
| | | AUC | Tubes included | N | AUC | Tubes included | N |
| Number of tubes included | 1 | 0.895 | 2$^{nd}$ | 2150 | 0.843 | 2$^{nd}$ | 2085 |
| | 2 | 0.894 | 2$^{nd}$, 4$^{th}$ | 2150 | 0.859 | 2$^{nd}$, 6$^{th}$ | 2085 |
| | 3 | 0.898 | 2$^{nd}$, 4$^{th}$, 7$^{th}$ | 2150 | 0.859 | 2$^{nd}$, 6$^{th}$, 7$^{th}$ | 2085 |
| | 4 | 0.899 | 2$^{nd}$, 4$^{th}$, 7$^{th}$, 9$^{th}$ | 2150 | 0.846 | 2$^{nd}$, 4$^{th}$, 6$^{th}$, 7$^{th}$ | 2085 |
| | 5 | 0.893 | 2$^{nd}$, 4$^{th}$, 6$^{th}$, 7$^{th}$, 9$^{th}$ | 2150 | 0.856 | 2$^{nd}$, 4$^{th}$, 6$^{th}$, 7$^{th}$, 11$^{th}$ | 2085 |
| | 6 | 0.893 | 2$^{nd}$, 3$^{rd}$, 4$^{th}$, 6$^{th}$, 7$^{th}$, 9$^{th}$ | 2150 | 0.864 | 2$^{nd}$, 4$^{th}$, 5$^{th}$, 6$^{th}$, 7$^{th}$, 11$^{th}$ | 2085 |
| | 7 | 0.894 | 2$^{nd}$, 3$^{rd}$, 4$^{th}$, 5$^{th}$, 6$^{th}$, 7$^{th}$, 9$^{th}$ | 2150 | 0.865 | 2$^{nd}$, 3$^{rd}$, 4$^{th}$, 5$^{th}$, 6$^{th}$, 7$^{th}$, 11$^{th}$ | 2085 |
| | 8 | 0.898 | 2$^{nd}$, 3$^{rd}$, 4$^{th}$, 5$^{th}$, 6$^{th}$, 7$^{th}$, 9$^{th}$, 12$^{th}$ | 2150 | 0.859 | 2$^{nd}$, 3$^{rd}$, 4$^{th}$, 5$^{th}$, 6$^{th}$, 7$^{th}$, 10$^{th}$, 11$^{th}$ | 2085 |
| | 9 | 0.901 | 2$^{nd}$, 3$^{rd}$, 4$^{th}$, 5$^{th}$, 6$^{th}$, 7$^{th}$, 9$^{th}$, 11$^{th}$, 12$^{th}$ | 2150 | 0.860 | 2$^{nd}$, 3$^{rd}$, 4$^{th}$, 5$^{th}$, 6$^{th}$, 7$^{th}$, 8$^{th}$, 10$^{th}$, 11$^{th}$ | 2085 |
| | 10 | 0.891 | 2$^{nd}$, 3$^{rd}$, 4$^{th}$, 5$^{th}$, 6$^{th}$, 7$^{th}$, 9$^{th}$, 10$^{th}$, 11$^{th}$, 12$^{th}$ | 2150 | 0.860 | 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$ | 2085 |

TABLE 9-continued

Tubes included in feature selection analysis.

| | | | | | | |
|---|---|---|---|---|---|---|
| 11 | 0.873 | $2^{nd}, 3^{rd}, 4^{th}, 5^{th}, 6^{th}, 7^{th}, 8^{th}, 9^{th}, 10^{th}, 11^{th}, 12^{th}$ | 2150 | 0.856 | $2^{nd}, 3^{rd}, 4^{th}, 5^{th}, 6^{th}, 7^{th}, 8^{th}, 9^{th}, 10^{th}, 11^{th}, 12^{th}$ | 2085 |
| 12 | 0.857 | $2^{nd}, 3^{rd}, 4^{th}, 5^{th}, 6^{th}, 7^{th}, 8^{th}, 9^{th}, 10^{th}, 11^{th}, 12^{th}, 13^{th}$ | 2150 | 0.848 | $2^{nd}, 3^{rd}, 4^{th}, 5^{th}, 6^{th}, 7^{th}, 8^{th}, 9^{th}, 10^{th}, 11^{th}, 12^{th}, 13^{th}$ | 2085 |
| 13 | 0.845 | $1^{st}, 2^{nd}, 3^{rd}, 4^{th}, 5^{th}, 6^{th}, 7^{th}, 8^{th}, 9^{th}, 10^{th}, 11^{th}, 12^{th}, 13^{th}$ | 2150 | 0.848 | $1^{st}, 2^{nd}, 3^{rd}, 4^{th}, 5^{th}, 6^{th}, 7^{th}, 8^{th}, 9^{th}, 10^{th}, 11^{th}, 12^{th}, 13^{th}$ | 2085 |

The markers measured in each tube are the same as that noted in Table 2, above.

Figure 9:
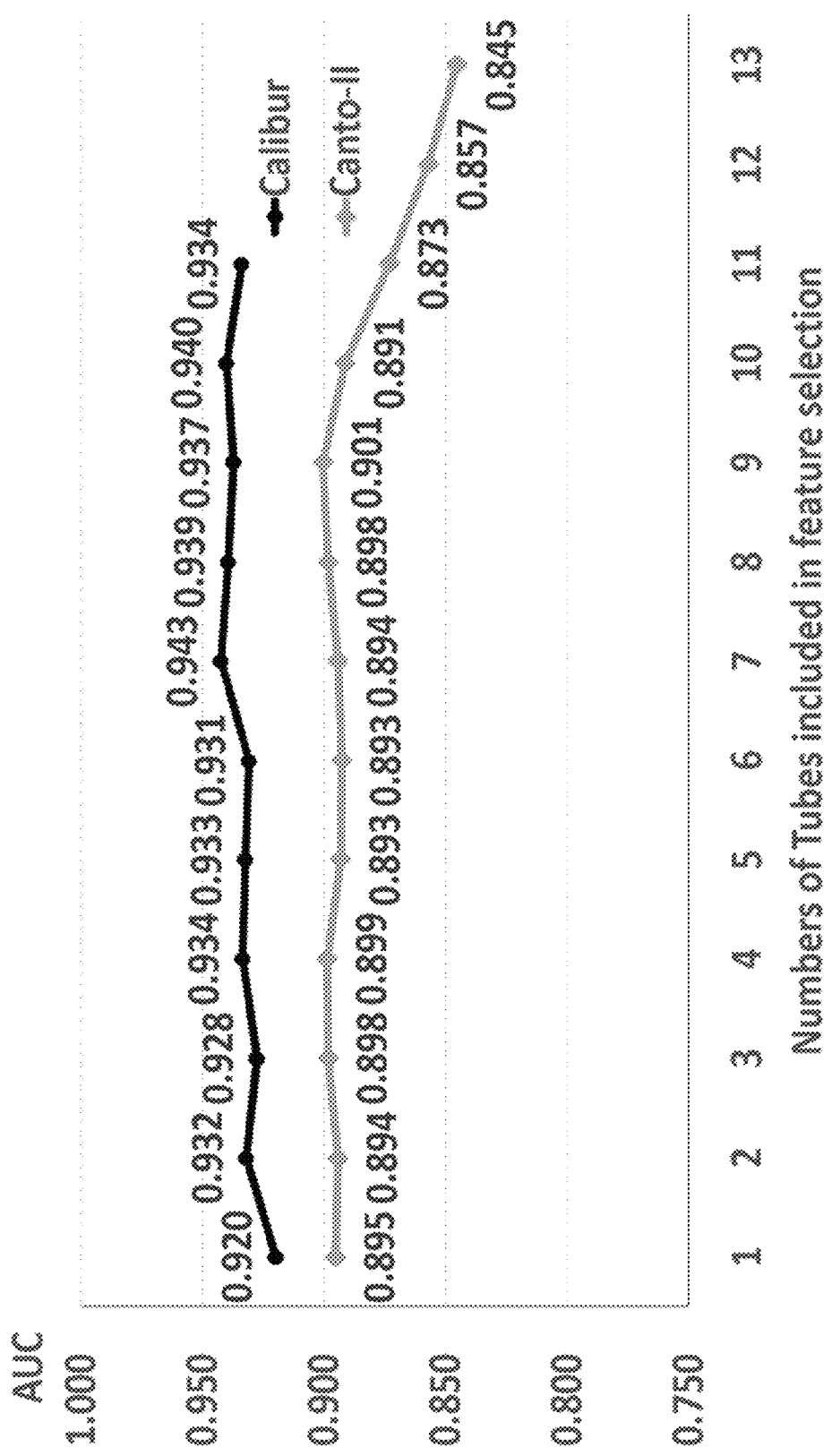
FIG. 9 illustrates a features selection analysis of abnormal vs. normal, in accordance with an exemplary embodiment.

FIG. 9 illustrates a features selection analysis of abnormal vs. normal, in accordance with the exemplary embodiment. Tubes included in each feature selection analysis experiments are listed in Table 9. Tubes included in each feature selection analysis experiments are listed in Table 9. The tube combinations of FIG. 9 may be as follows: 1: Calibur-5th tube (CD16, CD13 & CD45), Canto-II-2nd tube (HLA-DR, CD11b & CD45); 2: Calibur-5th & 11th tube (HLA-DR, CD34 & CD45), Canto-II-2nd & 4th tube (CD46, CD38 & CD45); 3: Calibur-5th & 9th (CD34, CD38 & CD45) & 11th tube, Canto-II-2nd & 4th & 7th tube (CD14, CD33 & CD45); 4: Calibur-2nd, 5th, 9th & 11th, Canto-II-2nd, 4th, 7th & 9th tube; 5: Calibur-2nd, 4th, 5th, 9th & 11th tube, Canto-II-2nd, 4th, 6th (CD15, CD34 & CD45), 7th & 9th tube.

As illustrated in FIG. 9, data from more than the best 2-tubes did not significantly improve AUC scores in Calibur (from 0.932 (2 tubes) to 0.934 (11 tubes)). In Canto-II, data from 4 tubes appeared adequate to obtain high AUC scores (from 0.899 (4 tubes) to 0.845 (13 tubes)). Accordingly, the hematological abnormality classifier could execute a binary classification well with a variable number of tubes.

Accordingly, a hematological abnormality classifier may utilize processed MFC data representing a GMM-based phenotype representation to rapidly classify specimens with a desirable accuracy and with desirable prognostic significance for AML patients after induction chemotherapy. Detecting MRD plays an important role in guiding decisions in treating hematological malignancies, because persistent detectable MRD usually indicates inadequate treatment and therefore implies poor prognosis. Although the manual gating may be a traditional process of MFC interpretation in clinical service, interpersonal variability during gating has been shown as a major factor affecting outcome prediction in flow-cytometry based experiments. Moreover, when MFC platforms may measure >100 parameters on a single-cell level, conventional 2D-plot manual gating may become a practically infeasible means to comprehensively present the information acquired in measured MFC data to physicians. Therefore, the hematological abnormality classifier can be more clinically-useful in supporting physicians to conduct MFC interpretation with high efficiency and fidelity than traditional manual gating.

As noted above, the hematological abnormality classifier may utilize processed MFC data with GMM as a background generative model. A probabilistic gradient-based approach (e.g., the Fisher scoring vector) may be utilized for deriving the high-dimensional MFC feature vector representation. This particular approach is both generative and discriminative. The feature vector may capture the variabilities and interacting information on multi-measurements per sample. The use of a vectorized approach may be important in achieving strong supervised hematological abnormality classifier training on large-scale data samples and may also speed up associated computation. Thus, the derivation of a phenotype representation that captures inherent variabilities in a high dimensional space in combination with maximum-boundary based optimization used in the processed MFC data provides better predictive power and a more robust classifier embodied in the hematological abnormality classifier of various embodiments.

Furthermore, the desirable performance of the hematological abnormality classifier is illustrated from the study sample set in the exemplary embodiment. As noted above in reference to the exemplary embodiment, three binary classification models for predicting AML-vs-normal, MDS-vs-normal, and abnormal-vs-normal were constructed, instead of a multi-class classification model. This is because AML and MDS can represent as a continuous disease spectrum rather than two distinct diseases, as mentioned before. Also, three binary classification systems were produced to address definite manual interpretation in MFC data. As noted above for the exemplary embodiment, the algorithm performance reached over 0.85 ACC in all of the binary classification tasks, suggesting a desirable consistency with manual analyses.

In summary, the hematological abnormality classifier is a powerful tool for automated MFC analysis on MRD detection in AML and MDS. It not only is a faster and reliable way for MFC data interpretation, but also possess a great advantage in its ability to integrate with other clinical tests including morphology, genomics, and cytogenetics for MRD detection and prognostic stratification.

While various embodiments of the invention have been described above, it should be understood that they have been presented by way of example only, and not by way of limitation. Likewise, the various diagrams may depict an example architectural or configuration, which are provided to enable persons of ordinary skill in the art to understand exemplary features and functions of the invention. Such persons would understand, however, that the invention is not restricted to the illustrated example architectures or configurations, but can be implemented using a variety of alternative architectures and configurations. Additionally, as would be understood by persons of ordinary skill in the art, one or more features of one embodiment can be combined with one or more features of another embodiment described herein. Thus, the breadth and scope of the present disclosure should not be limited by any of the above-described exemplary embodiments.

It is also understood that any reference to an element herein using a designation such as "first," "second," and so forth does not generally limit the quantity or order of those elements. Rather, these designations can be used herein as a convenient means of distinguishing between two or more elements or instances of an element. Thus, a reference to first and second elements does not mean that only two elements can be employed, or that the first element must precede the second element in some manner.

Additionally, a person having ordinary skill in the art would understand that information and signals can be represented using any of a variety of different technologies and techniques. For example, data, instructions, commands, information, signals, bits and symbols, for example, which may be referenced in the above description can be represented by voltages, currents, electromagnetic waves, magnetic fields or particles, optical fields or particles, or any combination thereof.

A person of ordinary skill in the art would further appreciate that any of the various illustrative logical blocks, modules, processors, means, circuits, methods and functions described in connection with the aspects disclosed herein can be implemented by electronic hardware (e.g., a digital implementation, an analog implementation, or a combination of the two, which can be designed using source coding or some other technique), various forms of program or design code incorporating instructions (which can be referred to herein, for convenience, as "software" or a "software module"), or combinations of both. To clearly illustrate this interchangeability of hardware and software, various illustrative components, blocks, modules, circuits, and steps have been described above generally in terms of their functionality. Whether such functionality is implemented as hardware, firmware or software, or a combination of these technique, depends upon the particular application and design constraints imposed on the overall system. Skilled artisans can implement the described functionality in various ways for each particular application, but such implementation decisions should not be interpreted as causing a departure from the scope of the present disclosure.

Furthermore, a person of ordinary skill in the art would understand that various illustrative logical blocks, modules, devices, components and circuits described herein can be implemented within or performed by an integrated circuit (IC) that can include a general purpose processor, a digital signal processor (DSP), an application specific integrated circuit (ASIC), a field programmable gate array (FPGA) or other programmable logic device, or any combination thereof. The logical blocks, modules, and circuits can further include antennas and/or transceivers to communicate with various components within the network or within the device. A general purpose processor can be a microprocessor, but in the alternative, the processor can be any conventional processor, controller, or state machine. A processor can also be implemented as a combination of computing devices, e.g., a combination of a DSP and a microprocessor, a plurality of microprocessors, one or more microprocessors in conjunction with a DSP core, or any other suitable configuration to perform the functions described herein.

If implemented in software, the functions can be stored as one or more instructions or code on a computer-readable medium. Thus, the steps of a method or algorithm disclosed herein can be implemented as software stored on a computer-readable medium. Computer-readable media includes both computer storage media and communication media including any medium that can be enabled to transfer a computer program or code from one place to another. A storage media can be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to store desired program code in the form of instructions or data structures and that can be accessed by a computer.

In this document, the term "module" as used herein, refers to software, firmware, hardware, and any combination of these elements for performing the associated functions described herein. Additionally, for purpose of discussion, the various modules are described as discrete modules; however, as would be apparent to one of ordinary skill in the art, two or more modules may be combined to form a single module that performs the associated functions according embodiments of the invention.

Additionally, memory or other storage, as well as communication components, may be employed in embodiments of the invention. It will be appreciated that, for clarity purposes, the above description has described embodiments of the invention with reference to different functional units and processors. However, it will be apparent that any suitable distribution of functionality between different functional units, processing logic elements or domains may be used without detracting from the invention. For example, functionality illustrated to be performed by separate processing logic elements, or controllers, may be performed by the same processing logic element, or controller. Hence, references to specific functional units are only references to a suitable means for providing the described functionality, rather than indicative of a strict logical or physical structure or organization.

Various modifications to the implementations described in this disclosure will be readily apparent to those skilled in the art, and the general principles defined herein can be applied to other implementations without departing from the scope of this disclosure. Thus, the disclosure is not intended to be limited to the implementations shown herein, but is to be accorded the widest scope consistent with the novel features and principles disclosed herein, as recited in the claims below.

What is claimed is:

1. A system comprising:
at least one processor operatively coupled with a datastore, the at least one processor configured to:
receive, from a flow cytometer that is designed to measure multiple parameters, a flow cytometry data matrix that characterizes a tube,
wherein the flow cytometry data matrix includes values that are generated by the flow cytometer via analysis of scattering of light by particles in the tube,
wherein each of the values characterizes a different one of the particles, and
wherein a sample is comprised of a plurality of tubes;
convert the flow cytometry data matrix into a tube high-dimensional vector,
wherein the tube high-dimensional vector is a tube-level feature vector that concatenates the multiple parameters measured by the flow cytometer;
produce a sample high-dimensional vector that comprises a concatenation of a plurality of tube high-dimensional vectors associated with the sample;
assemble a training data set comprising a plurality of sample high-dimensional vectors;
receive, from the datastore, outcome information comprising respective labels associated with each sample high-dimensional vector of the plurality of sample high-dimensional vectors; and train a classifier based on the training data set and the outcome information.

2. The system of claim 1, wherein the at least one processor is further configured to:

determine an outcome for a new sample based on applying the classifier to the new sample.

3. The system of claim 1, wherein the at least one processor is further configured to:

determine an outcome for a new sample high-dimensional vector associated with a new sample by applying the classifier that is trained based on the training dataset and the outcome information to the new second sample high-dimensional vector associated with the new sample.

4. The system of claim 1, wherein the sample is derived from blood, mucus, bone marrow, or other fluids containing cells from a person.

5. The system of claim 1, wherein the respective labels characterize whether each of the second plurality of high-dimensional vectors is normal or abnormal.

6. The system of claim 1, wherein the respective labels characterize whether each sample high-dimensional vector of the plurality of sample high-dimensional vectors is indicative of a hematological malignancy.

7. The system of claim 1, wherein the classifier is trained using support vector machines.

8. The system of claim 1, wherein the at least one processor is further configured to:

convert the flow cytometry data matrix into the tube high-dimensional vector using Fisher vector encoding and a gaussian mixture model distribution.

9. The system of claim 1, wherein the at least one processor is further configured to:

convert the flow cytometry data matrix into the tube high-dimensional vector by modeling the flow cytometry data matrix with a generative probability distribution.

10. A method performed by a computing device, the method comprising:

separating a sample set into a training data set and a validation data set;

receiving a flow cytometry data matrix that characterizes a tube, wherein the flow cytometry data matrix includes values that are generated via analysis of scattering of light by particles in the tube, wherein each of the values characterizes a different one of the particles, and wherein a sample is comprised of a plurality of tubes;

converting the flow cytometry data matrix into a tube high-dimensional vector, wherein the tube high-dimensional vector is a tube-level feature vector that concatenates parameters that are measured by a flow cytometer to produce the flow cytometry data matrix;

producing a sample high-dimensional vector that comprises a concatenation of a plurality of tube high-dimensional vectors associated with the sample;

separating a plurality of sample high-dimensional vectors into the training data set and the validation data set, wherein the training data set comprises a first subset of the plurality of sample high-dimensional vectors, and wherein the validation data set comprises a second subset of the plurality of sample high-dimensional vectors;

receiving training outcome information of the training data set comprising respective training outcome labels for each of the first subset of the plurality of sample high-dimensional vectors;

training a classifier based on the training data set and the training outcome information;

receiving validation outcome information of the validation data set comprising respective validation outcome labels for each of the second subset of the plurality of sample high-dimensional vectors; and determining an accuracy value for the classifier based on the validation data set and the validation outcome information.

11. The method of claim 10, wherein the plurality of tube high-dimensional vectors are associated with respective tubes of the sample.

12. The method of claim 10, wherein the plurality of sample high-dimensional vectors are associated with respective samples.

13. The method of claim 10, wherein the concatenation of the plurality of tube high-dimensional vectors is produced in a predetermined manner of concatenation.

14. The method of claim 10, wherein the computing device is the flow cytometer.

15. A non-transitory computer readable medium having instructions stored thereon, wherein the instructions, when executed by a processor, cause a device to perform operations comprising:

receiving a flow cytometry data matrix that characterizes a tube, wherein the flow cytometry data matrix includes values that are generated by a flow cytometer via analysis of scattering of light by particles in tube, wherein each of the values characterizes a different one of the particles, and wherein a sample is comprised of at least one tube;

converting the flow cytometry data matrix into a tube high-dimensional vector, wherein the tube high-dimensional vector is a tube-level feature vector that concatenates parameters that are measured by the flow cytometer to produce the flow cytometry data matrix;

producing a sample high-dimensional vector that comprises a concatenation of a plurality of tube high-dimensional vectors associated with the sample;

assembling a training data set comprising a plurality of sample high-dimensional vectors;

receiving outcome information comprising respective labels associated with each of the plurality of sample high-dimensional vectors; and training a classifier based on the training data set and the outcome information.

16. The non-transitory computer readable medium of claim 15, wherein the operations further comprise:

receiving the flow cytometry data matrix from over a network.

17. A non-transitory computer readable medium having instructions stored thereon, wherein the instructions, when executed by a processor, cause a device to perform operations comprising:

receiving a flow cytometry data matrix that characterizes a tube, wherein the flow cytometry data matrix includes values that are generated by a flow cytometer via analysis of scattering of light by particles in the tube, wherein each of the values characterizes a different one of the particles, and wherein a sample is comprised of at least one or a plurality of tubes;

converting the flow cytometry data matrix into a tube high-dimensional vector, wherein the tube high-dimensional vector is a tube-level feature vector that concatenates parameters measured by the flow cytometer;

producing a sample high-dimensional vector that comprises a concatenation of a plurality of tube high-dimensional vectors associated with the sample;

separating a plurality of sample high-dimensional vectors into a training data set and a validation data set, wherein the training data set comprises a first subset of the plurality of sample high-dimensional vectors, and wherein the validation data set comprises a second subset of the plurality of sample high-dimensional vectors;

receiving training outcome information comprising respective training outcome labels for each of the first subset of the plurality of sample high-dimensional vectors;

training a classifier based on the training data set and the training outcome information;

receiving validation outcome information of the validation data set comprising respective validation outcome labels for each of the second subset of the plurality of sample high-dimensional vectors; and determining an accuracy value for the classifier based on the validation data set and the validation outcome information.

18. The non-transitory computer readable medium of claim 17, wherein the validation data set comprises multiple validation high-dimensional vectors associated with validation samples and the validation outcome information comprises respective validation outcome labels associated with each of the multiple validation high-dimensional vectors.

19. The non-transitory computer readable medium of claim 17, wherein the operations further comprise:

training the classifier based on an expanded training data set with a greater number of samples than the training data set in response to the accuracy value falling below a threshold value.

* * * * *